(12) United States Patent
Jarrell et al.

(10) Patent No.: US 11,842,891 B2
(45) Date of Patent: Dec. 12, 2023

(54) ION DETECTOR

(71) Applicant: Waters Technologies Corporation, Milford, MA (US)

(72) Inventors: Joseph A. Jarrell, Newton Highlands, MA (US); Martin Gilar, Franklin, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 17/225,514

(22) Filed: Apr. 8, 2021

(65) Prior Publication Data

US 2021/0319994 A1    Oct. 14, 2021

Related U.S. Application Data

(60) Provisional application No. 63/007,691, filed on Apr. 9, 2020.

(51) Int. Cl.
| | |
|---|---|
| *H01J 49/02* | (2006.01) |
| *G01N 27/623* | (2021.01) |
| *H01J 49/00* | (2006.01) |
| *H01J 49/16* | (2006.01) |
| *H01J 49/40* | (2006.01) |
| *G01N 30/62* | (2006.01) |

(52) U.S. Cl.
CPC ......... *H01J 49/025* (2013.01); *G01N 27/623* (2021.01); *G01N 30/62* (2013.01); *H01J 49/0031* (2013.01); *H01J 49/164* (2013.01); *H01J 49/40* (2013.01)

(58) Field of Classification Search
CPC .... H01J 49/025; H01J 49/0031; H01J 49/164; H01J 49/40; G01N 27/623; G01N 27/622; G01N 33/6848; G01N 30/62
USPC ................................ 250/397, 283, 286, 287
See application file for complete search history.

(56) References Cited

U.S. PATENT DOCUMENTS

| | | | |
|---|---|---|---|
| 5,770,857 A | 6/1998 | Fuerstenau et al. | |
| 5,880,466 A | 3/1999 | Benner | |
| 6,480,278 B1 | 11/2002 | Fuerstenau et al. | |
| 6,576,899 B2 | 6/2003 | Sinha et al. | |
| 6,744,042 B2 | 6/2004 | Zajfman et al. | |
| 6,747,272 B2 | 6/2004 | Takahashi | |
| 6,753,523 B1 | 6/2004 | Whitehouse et al. | |
| 6,858,840 B2 | 2/2005 | Berkout et al. | |
| 6,888,130 B1 | 5/2005 | Gonin | |

(Continued)

FOREIGN PATENT DOCUMENTS

| | | |
|---|---|---|
| CN | 1836308 A | 9/2006 |
| CN | 101151704 A | 3/2008 |

(Continued)

OTHER PUBLICATIONS

Arroyo, J.O., et al., "Interferometric scattering microscopy and its combination with single-molecule fluorescence imaging", Nature Protocols, 11(4):617-633 (2016).

(Continued)

*Primary Examiner* — Kiet T Nguyen
(74) *Attorney, Agent, or Firm* — Goodwin Procter LLP

(57) ABSTRACT

An ion detector comprises a surface configured to receive one or more ions and a detector configured to detect one or more ions by detecting electromagnetic radiation scattered by one or more ions at the surface.

12 Claims, 2 Drawing Sheets

(56) References Cited

U.S. PATENT DOCUMENTS

| | | |
|---|---|---|
| 6,967,326 B2 | 11/2005 | Pai et al. |
| 6,987,264 B1 | 1/2006 | Whitehouse et al. |
| 7,002,166 B2 | 2/2006 | Jamieson et al. |
| RE39,099 E | 5/2006 | Krutchinsky et al. |
| 7,078,679 B2 | 7/2006 | Westphall et al. |
| 7,161,146 B2 | 1/2007 | Doroshenko et al. |
| 7,170,053 B2 | 1/2007 | Shvartsburg et al. |
| 7,176,455 B1 | 2/2007 | Whitehouse et al. |
| 7,217,919 B2 | 5/2007 | Boyle et al. |
| 7,361,888 B1 | 4/2008 | Boyle et al. |
| 7,365,314 B2 | 4/2008 | Lee et al. |
| 7,385,187 B2 | 6/2008 | Verentchikov et al. |
| 7,482,581 B2 | 1/2009 | Lange et al. |
| 7,482,582 B2 | 1/2009 | Raznikov et al. |
| 7,547,878 B2 | 6/2009 | Schultz et al. |
| 7,564,026 B2 | 7/2009 | Vestal |
| 7,608,817 B2 | 10/2009 | Flory |
| 7,820,961 B2 | 10/2010 | Hashimoto et al. |
| 7,829,842 B2 | 11/2010 | Makarov |
| 7,858,926 B1 | 12/2010 | Whitehouse et al. |
| 7,880,136 B2 | 2/2011 | Makarov et al. |
| 7,888,633 B2 | 2/2011 | Franzen et al. |
| 7,952,070 B2 | 5/2011 | Senko et al. |
| 7,960,690 B2 | 6/2011 | Schwartz et al. |
| 7,982,871 B2 | 7/2011 | Caro et al. |
| 8,101,910 B2 | 1/2012 | Loboda |
| 8,115,165 B2 | 2/2012 | Thomson |
| 8,237,111 B2 | 8/2012 | Golikov et al. |
| 8,278,115 B2 | 10/2012 | Coon et al. |
| 8,294,085 B2 | 10/2012 | Ding |
| 8,294,086 B2 | 10/2012 | Holle |
| 8,319,180 B2 | 11/2012 | Nikolaev et al. |
| 8,334,504 B2 | 12/2012 | Finlay et al. |
| 8,395,112 B1 | 3/2013 | Bier |
| 8,399,827 B1 | 3/2013 | Grothe |
| 8,455,815 B2 | 6/2013 | Steiner et al. |
| 8,586,918 B2 | 11/2013 | Brucker et al. |
| 8,664,590 B2 | 3/2014 | Ding et al. |
| 8,796,619 B1 | 8/2014 | Doroshenko et al. |
| 8,829,432 B2 | 9/2014 | Stein |
| 8,853,620 B2 | 10/2014 | Lange |
| 8,921,772 B2 | 12/2014 | Verenchikov |
| 8,921,779 B2 | 12/2014 | Grothe, Jr. |
| 8,933,397 B1 | 1/2015 | Hanson |
| 8,963,075 B2 | 2/2015 | Chen et al. |
| 9,000,364 B2 | 4/2015 | Ermakov et al. |
| 9,018,580 B2 | 4/2015 | Lemoine et al. |
| 9,035,245 B2 | 5/2015 | Glasmachers et al. |
| 9,043,164 B2 | 5/2015 | Makarov |
| 9,136,102 B2 | 9/2015 | Grinfeld et al. |
| 9,224,586 B2 | 12/2015 | Chen et al. |
| 9,299,546 B2 | 3/2016 | Nikolaev |
| 9,312,119 B2 | 4/2016 | Verenchikov |
| 9,324,547 B2 | 4/2016 | Hauschild et al. |
| 9,324,551 B2 | 4/2016 | Taniguchi et al. |
| 9,349,579 B2 | 5/2016 | Kholomeev et al. |
| 9,366,650 B2 | 6/2016 | Knochenmuss |
| 9,368,336 B2 | 6/2016 | Xu et al. |
| 9,396,923 B2 | 7/2016 | Kodera et al. |
| 9,455,128 B2 | 9/2016 | Remes et al. |
| 9,460,905 B2 | 10/2016 | Aizikov et al. |
| 9,520,280 B2 | 12/2016 | Makarov |
| 9,543,131 B2 | 1/2017 | Kuehn et al. |
| 9,548,195 B2 | 1/2017 | Hock et al. |
| 9,666,423 B2 | 5/2017 | Benner |
| 9,714,919 B2 | 7/2017 | Brucker et al. |
| 9,779,930 B2 | 10/2017 | Guna |
| 9,786,483 B2 | 10/2017 | Heeren et al. |
| 9,911,587 B1 | 3/2018 | Li et al. |
| 9,911,588 B1 | 3/2018 | Li |
| 9,922,812 B2 | 3/2018 | Makarov |
| 9,972,480 B2 | 5/2018 | Ristroph |
| 9,972,483 B2 | 5/2018 | Makarov |
| 10,014,168 B2 | 7/2018 | Zhang et al. |
| 10,020,174 B2 | 7/2018 | Zhang et al. |
| 10,032,617 B2 | 7/2018 | Welkie |
| 10,141,176 B2 | 11/2018 | Stewart et al. |
| 10,145,792 B2 | 12/2018 | Jungwirth et al. |
| 10,147,591 B2 | 12/2018 | Derrick et al. |
| 10,186,409 B2 | 1/2019 | Youngner |
| 10,229,823 B2 | 3/2019 | Nishiguchi et al. |
| 10,242,854 B2 | 3/2019 | Rusinov et al. |
| 10,276,361 B2 | 4/2019 | Grinfeld et al. |
| 10,297,436 B2 | 5/2019 | Tsybin et al. |
| 10,304,672 B2 | 5/2019 | Fedosenko et al. |
| 10,340,052 B2 | 7/2019 | Jungwirth et al. |
| 10,453,668 B2 | 10/2019 | Continetti et al. |
| 10,510,524 B2 | 12/2019 | Sekiya et al. |
| 10,580,633 B2 | 3/2020 | Cooks et al. |
| 10,580,636 B2 | 3/2020 | Chutjian et al. |
| 10,585,103 B2 | 3/2020 | Jarrold et al. |
| 10,593,525 B2 | 3/2020 | Hock et al. |
| 10,620,121 B2 | 4/2020 | Zheng et al. |
| 10,622,203 B2 | 4/2020 | Veryovkin et al. |
| 10,734,210 B2 | 8/2020 | Stewart |
| 10,755,907 B2 | 8/2020 | Aizikov et al. |
| 10,872,755 B2 | 12/2020 | Christian |
| 10,903,061 B2 | 1/2021 | Kholomeev et al. |
| 10,937,638 B2 | 3/2021 | Cooks et al. |
| 10,984,999 B2 | 4/2021 | Hsieh et al. |
| 11,024,491 B2 | 6/2021 | Giannakopulos et al. |
| 11,069,516 B2 | 7/2021 | Baba et al. |
| 11,075,067 B2 | 7/2021 | Takahashi et al. |
| 11,107,670 B2 | 8/2021 | Aliman et al. |
| 11,127,581 B2 | 9/2021 | Cooks et al. |
| 11,131,655 B2 | 9/2021 | Thoeing et al. |
| 11,145,503 B2 | 10/2021 | Dziekonski |
| 11,152,198 B2 | 10/2021 | Shaw |
| 11,177,122 B2 | 11/2021 | Jarrold et al. |
| 11,367,602 B2 | 6/2022 | Richardson et al. |
| 2002/0178923 A1 | 12/2002 | Kishovich et al. |
| 2007/0221862 A1 | 9/2007 | Suits et al. |
| 2008/0191130 A1 | 8/2008 | Bateman et al. |
| 2009/0076535 A1 | 3/2009 | Agrawal et al. |
| 2010/0032561 A1 | 2/2010 | Giles et al. |
| 2010/0059673 A1 | 3/2010 | Makarov et al. |
| 2010/0176291 A1 | 7/2010 | Hager et al. |
| 2010/0294924 A1* | 11/2010 | Brouard .............. H01J 49/0045 250/282 |
| 2012/0068068 A1* | 3/2012 | Hill .................. H01J 37/244 250/307 |
| 2012/0112056 A1 | 5/2012 | Brucker et al. |
| 2013/0270433 A1 | 10/2013 | Ding et al. |
| 2013/0306855 A1* | 11/2013 | Raptakis .............. H01J 49/025 250/282 |
| 2014/0061460 A1 | 3/2014 | Hauschild et al. |
| 2015/0228469 A1 | 8/2015 | Mizutani |
| 2015/0318161 A1 | 11/2015 | Brown et al. |
| 2016/0018373 A1 | 1/2016 | Pagé et al. |
| 2016/0035555 A1 | 2/2016 | Hanson |
| 2016/0379814 A1 | 12/2016 | Yamada et al. |
| 2017/0098534 A1 | 4/2017 | Brown et al. |
| 2017/0365458 A1 | 12/2017 | Collins et al. |
| 2018/0005809 A1 | 1/2018 | Roukes et al. |
| 2018/0247805 A1 | 8/2018 | Continetti et al. |
| 2018/0275097 A1 | 9/2018 | Sandoghdar et al. |
| 2019/0066989 A1 | 2/2019 | Cooks et al. |
| 2019/0164735 A1 | 5/2019 | Yip et al. |
| 2020/0043716 A1 | 2/2020 | Taniguchi |
| 2020/0075300 A1 | 3/2020 | Bern |
| 2020/0161119 A1 | 5/2020 | Richardson et al. |
| 2020/0249240 A1 | 8/2020 | Jarrold et al. |
| 2020/0300630 A1 | 9/2020 | Kozuma et al. |
| 2020/0357622 A1 | 11/2020 | Arnold et al. |
| 2020/0357626 A1 | 11/2020 | Jarrold et al. |
| 2021/0013022 A1 | 1/2021 | Tateishi |
| 2021/0050200 A1 | 2/2021 | Song et al. |
| 2021/0134573 A1 | 5/2021 | Hager |
| 2021/0166831 A1 | 6/2021 | Cao |
| 2021/0193447 A1 | 6/2021 | Jarrold et al. |
| 2021/0202225 A1 | 7/2021 | Jarrold et al. |
| 2021/0210331 A1 | 7/2021 | Senko et al. |
| 2021/0210332 A1 | 7/2021 | Jarrold et al. |
| 2021/0210335 A1 | 7/2021 | Jarrold |

(56) References Cited

U.S. PATENT DOCUMENTS

| | | |
|---|---|---|
| 2021/0217606 A1 | 7/2021 | Jarrold et al. |
| 2021/0225625 A1 | 7/2021 | Cooks et al. |
| 2021/0262915 A1 | 8/2021 | Stevens et al. |
| 2021/0272790 A1 | 9/2021 | Stewart et al. |
| 2021/0287892 A1 | 9/2021 | Lehmann |
| 2021/0287897 A1 | 9/2021 | Lange |
| 2021/0327605 A1 | 10/2021 | Shen et al. |
| 2021/0335592 A1 | 10/2021 | Cooks et al. |
| 2021/0343518 A1 | 11/2021 | Pophristic |

FOREIGN PATENT DOCUMENTS

| | | |
|---|---|---|
| CN | 102169791 A | 8/2011 |
| CN | 102648511 A | 8/2012 |
| CN | 103548111 A | 1/2014 |
| CN | 103745905 A | 4/2014 |
| CN | 104766780 A | 7/2015 |
| DE | 19605100 A1 | 8/1996 |
| EP | 1665326 B1 | 4/2010 |
| EP | 1665328 B1 | 6/2012 |
| EP | 1549914 B1 | 12/2012 |
| EP | 2665084 A2 | 11/2013 |
| EP | 2884520 B1 | 2/2018 |
| EP | 3340276 A1 | 6/2018 |
| EP | 2951851 B1 | 10/2019 |
| EP | 2856139 B1 | 1/2020 |
| EP | 3505489 B1 | 3/2020 |
| EP | 3289603 B1 | 12/2020 |
| EP | 3884510 A1 | 9/2021 |
| EP | 3891777 A1 | 10/2021 |
| EP | 3895202 A1 | 10/2021 |
| EP | 3895203 A1 | 10/2021 |
| EP | 3440691 B1 | 11/2021 |
| FR | 3010527 A1 | 3/2015 |
| GB | 2434249 A | 7/2007 |
| GB | 2470133 A | 11/2010 |
| GB | 2598591 A | 3/2022 |
| JP | 2015170445 A | 9/2015 |
| NO | 2020219605 A1 | 10/2020 |
| WO | 9931707 A1 | 6/1999 |
| WO | 2002103747 A1 | 12/2002 |
| WO | 2003098190 A2 | 11/2003 |
| WO | 2005041244 A2 | 5/2005 |
| WO | 2008071967 A2 | 6/2008 |
| WO | 2011086430 A1 | 7/2011 |
| WO | 2012083031 A1 | 6/2012 |
| WO | 2012092457 A1 | 7/2012 |
| WO | 2013143349 A1 | 10/2013 |
| WO | 2014183105 A1 | 11/2014 |
| WO | 2015097462 A1 | 7/2015 |
| WO | 2016073850 A1 | 5/2016 |
| WO | 2017089991 A1 | 6/2017 |
| WO | 2017190031 A1 | 11/2017 |
| WO | 2017196863 A1 | 11/2017 |
| WO | 2017214037 A1 | 12/2017 |
| WO | 2018011591 A1 | 1/2018 |
| WO | 2018109920 A1 | 6/2018 |
| WO | 2018124861 A2 | 7/2018 |
| WO | 2019016571 A1 | 1/2019 |
| WO | 2019060538 A1 | 3/2019 |
| WO | 2019140233 A1 | 7/2019 |
| WO | 2019162687 A1 | 8/2019 |
| WO | 2019202338 A1 | 10/2019 |
| WO | 2019231854 A1 | 12/2019 |
| WO | 2019236139 A1 | 12/2019 |
| WO | 2019236140 A1 | 12/2019 |
| WO | 2019236141 A1 | 12/2019 |
| WO | 2019236142 A1 | 12/2019 |
| WO | 2019236143 A1 | 12/2019 |
| WO | 2019236572 A1 | 12/2019 |
| WO | 2019236574 A1 | 12/2019 |
| WO | 2019243083 A1 | 12/2019 |
| WO | 2020049165 A1 | 3/2020 |
| WO | 2020106310 A1 | 5/2020 |
| WO | 2020117292 A1 | 6/2020 |
| WO | 2020121166 A1 | 6/2020 |
| WO | 2020121167 A1 | 6/2020 |
| WO | 2020157654 A1 | 8/2020 |
| WO | 2020157655 A1 | 8/2020 |
| WO | 2020157656 A1 | 8/2020 |
| WO | 2020198124 A1 | 10/2020 |
| WO | 2020198332 A1 | 10/2020 |
| WO | 2020219527 A1 | 10/2020 |
| WO | 2021006811 A1 | 1/2021 |
| WO | 2021061650 A1 | 4/2021 |
| WO | 2021072186 A1 | 4/2021 |
| WO | 2021084339 A1 | 5/2021 |
| WO | 2021126971 A1 | 6/2021 |
| WO | 2021126972 A1 | 6/2021 |
| WO | 2021144737 A1 | 7/2021 |
| WO | 2021158603 A1 | 8/2021 |
| WO | 2021158676 A1 | 8/2021 |
| WO | 2023111538 A1 | 6/2023 |

OTHER PUBLICATIONS

Austin, D.E., "Impact-Ionization Mass Spectrometry of Cosmic Dust", Dissertation California Institute of Technology (2003) 192 pages.

Barney, B.L., "A multi-stage image charge detector made from printed circuit boards", Review of Scientific Instruments 84:114101-1 through 114101-6 (2013).

Benner, W.H., "A Gated Electrostatic Ion Trap To Repetitiously Measure the Charge and m/z of Large Electrospray Ions", Anal. Chem 69:4162-4268 (1997).

Botamanenko, D.Y., et al., "Ion-Ion Interactions in Charge Detection Mass Spectrometry", J. Am. Soc. Mass Spectrom, [online] Nov. 1, 2019 DOI: 10.101007/s13361-019-02343-y.

Brown, B.A., et al., "Charge Detection Mass Spectrometry Measurements of Exosomes and other Extracellular Particles Enriched from Bovine Milk", Analytical Chemistry Just Accepted Manuscript DOI: 10.1021/acs.analchem.9b05173 Jan. 28, 2020.

Brunner, T., et al., "An RF-only ion-funnel for extraction from high-pressure gases", International Journal of Mass Spectrometry 379:110-120 (2015).

Cole, D., et al., "Label-Free Single-Molecule Imaging with Numerical-Aperture-Shaped Interferometric Scattering Microscopy", ACS Photonics 4:211-216 (2017).

Contino, N.C., "Ion Trap Charge Detection Mass Spectrometry: Lowering Limits of Detection and Improving Signal to Noise", Dissertation for Doctor of Philosophy at Indiana University (2013). 205 pages.

Contino, N.C., and Jarrold, M.F., "Charge detection mass spectrometry for single ions with a limit of detection of 30 charges", International Journal of Mass Spectrometry 345-347:153-159 (2013).

Contino, N.C., et al., "Charge Detection Mass Spectrometry with Resolved Charge States", J. Am. Soc. Mass Spectrom 24:101-108 (2013).

Curtis, A.S.G., "The Mechanism of Adhesion of Cells to Glass: A Study by Interference Reflection Microscopy", Journal of Cell Biology 20:199-215 (1964).

Dahan, M., et al., "A new type of electrostatic ion trap for storage fo fast ion beams", Rev. Sci. Instrum. 69(1):76-83 (1998).

Dania, Lorenzo "Investigation on a two-frequency Paul trap for a cavity optomechanics system", Master Thesis Università Degli Studi Di Pisa (2016-17) 89 pages.

Elliott, A.G., et al., "Simultaneous Measurements of Mass and Collisional Cross-Section of Single Ions with Charge Detection Mass Spectrometry", Analytical Chemistry 89:7701-7708 (2017).

Doussineau, T., et al., "Charge Detection Mass Spectrometry for the Characterization of Mass and Surface Area of Composite Nanoparticles", Journal of Physical Chemistry C 119:10844-10849 (2015).

Doussineau, T., et al., "Mass spectrometry investigations of nanoparticles by tandem charge detection mass spectrometry", SpectroscopyEurope 24(4) 3 pages (2012).

Doussineau, T., et al., "Charging megadalton poly(ethylene oxide)s by electrospray ionization. A charge detection mass spectrometry study", Rapid Communications in Mass Spectrometry 25:617-623 (2011).

(56) References Cited

OTHER PUBLICATIONS

Doussineau, T., et al., "Direct Molar Mass Determination of Self-Assembled Amphiphilic Block Copolymer Nanoobjects Using Electrospray-Charge Detection Mass Spectrometry", ACS Macro Lett 1:414-417 (2012).

Doussineau, T., et al., "Infrared multiphoton dissociation tandem charge detection-mass spectrometry of single megadalton electrosprayed ions", Review of Scientific Instruments 82:084104-1 through -8 (2011).

Doussineau, T., et al., "Pushing the Limit of Infrared Multiphoton Dissociation to Megadalton-Size DNA Ions", The Journal of Physical Chemistry Letters 3:2141-2145 (2012).

Draper, B.E., and Jarrold, M.F., "Real-Time Analysis and Signal Optimization for charge Detection Mass Spectrometry", J. Am. Soc., Mass Spectrom. 30:898-904 (2019).

Draper, B.E., et al., "The FUNPET—a New Hybrid Ion Funnel-Ion Carpet Atmospheric Pressure Interface for the Simultaneous Transmission of a Broad Mass Range", J. Am. Soc. Mass Spectrom Electronic Supplmentary Material [online]. Retrieved from Internet URL: (https://doi.org/10.1007/s13361-018-2038-3) 13 pages (2018).

Dunbar, C.A., et al., "Probing Antibody Binding to Canine Parvovirus with Charge Detection Mass Spectrometry", Journal of the American Chemical Society 140:15701-15711 (2018).

Dziekonski, E.T., et al., "Determination of Collision Cross Sections Using a Fourier Transform Electrostatic Linear Ion Trap Mass Spectrometer", J. Am. Soc. Mass Spectrom. 29:242-250 (2018).

Dziekonski, E.T., et al., "Fourier-Transform MS and Closed-Path Multireflection Time-of-Flight MS Using an Electrostatic Linear Ion Trap", Analytical Chemistry 89:10965-10972 (2017).

Elliot, A.G., et al., "Mass, mobility and MSn measurements of single ions using charge detection mass spectrometry", Analyst 142:2760-2759 (2017).

Elliott, A.G., et al., "Single Particle Analyzer of Mass: A Charge Detection Mass Spectrometer with a Multi-Detector Electrostatic Ion Trap", International Journal of Mass Spectrometry, 414:45-55 (2017).

Esser, T., "A Cryogenic Mass Spectrometer for Action Spectroscopy of Single Nanoparticles", Dissertation Universität Leipzig Jan. 21, 2019 198 pages.

Esser, T.K., et al., "A cryogenic single nanoparticle action spectrometer", Review of Scientific Instruments, 90:125110 (1990), 9 pages.

Fuerstenau, S.D., et al., "Mass Spectrometry of an Intact Virus" Angew. Chem Int. Ed. 40(3):541-544 (2001).

Gamero-Castaño, M., "Induction charge detector with multiple sensing stages", Review of Scientific Instruments 78:043301-7 (2007).

Goldfain, A.M., et al., "Dynamic Measurements of the Position, Orientation, and DNA Content of Individual Unlabeled Bacteriophages", Journal of Physical Chemistry B, 120:6130-6138 (2016).

Halim, M.A., et al., "Infrared Laser Dissociation of Single Megadalton Polymer Ions in a Gated Electrostatic Ion Trap. The Added Value of Statistical Analysis of Individual Events" Electronic Supplementary material (ESI) for Physical Chemistry Chemical Physics (2018) 10 pages.

Han, K.Y., and Ha, T., "Measuring molecular mass with light", Nature Photonics 12:378-385 (2018).

Hao, Z., et al., "Intact Antibody Characterization Using Orbitrap Mass Spectrometry", Chapter 10 in State-of-the-Art and Emerging Technologies for Therapeutic Monoclonal Antibody Characterization vol. 3. Defining the Next Generation of Analytical and Biophysical Techniques, DOI: 10.1021/bk-2015-1202, (2015).

Harper, C.C., et al., "Multiplexed Charge Detection Mass Spectrometry for High-Throughput Single Ion Analysis of Large Molecules", Analytical Chemistry 91:7458-7465 (2019).

Hogan, J.A., and Jarrold, M.F., "Optimized Electrostatic Linear Ion Trap for Charge Detection Mass Spectrometry", American Society for Mass Spectrometry DOI: 10.1007/s13361-018-2007-x (2018). 10 pages.

Hogan, Joanna Arielle, "Improving Charge Detection Mass Spectrometry Instrumentation for the Analysis of Heterogeneous, Multi-Megadalton Ions", Doctor of Philosophy Indiana University (2018) 207 pages.

Holmes, K., et al., "Assembly pathway of hepatitis B core virus-like particles from genetically fused dimers", JBC Papers in Press Manuscript M114.622035 (2015) 18 pages.

Howder, C.R., et al., "Optically detected, single nanoparticle mass spectrometer with pre-filtered electrospray nanoparticle source", Review of Scientific Instruments 85:014104-1 through -6 (2014). 6 pages.

Jarrold, M.F., "Helices and Sheets in vacuo" Physical Chemistry Chemical Physics 9:1659-1671 (2007).

Kaplan, P.D., et al.,, "Light-scattering microscope", Applied Optics 38(19):4151-4257 (1999).

Keifer, D.Z., "Charge detection mass spectrometry: weighing heavier things", Analyst 142:1654-1671 (2017).

Keifer, D.Z., and Jarrold, M.F., "Single-Molecule Mass Spectrometry", Mass Spectrometry Reviews DOI 10.1002/mas (2016). 19 pages.

Keifer, D.Z., et al., "Charge Detection Mass Spectrometry with Almost Perfect Charge Accuracy", Analytical Chemistry 87:10330-10337 (2015).

Keifer, D.Z., et al., "Measurement of the accurate mass of a 50 MDa infections virus", Rapid Communications in Mass Spectrometry 30:1957-1962 (2016).

Keifer, D.Z., et al., "Spontaneous Mass and Charge Losses from Single Multi-Megadalton Ions Studied by Charge Detection Mass Spectrometry", J. Am. Soc. Mass Spectrom. DOI: 10.1007/s13361-016-1582-y (2017). 9 pages.

Kondylis, P., et al., "Analytical Techniques to characterize the Structure, Properties, and Assembly of Virus Capsids", Analytical Chemistry 91:622-636 (2019).

Shinholt, Deven Lee, "Charge Detection Mass Spectrometry and a Frequency Scanned linear Quadrupole: Mass Analysis of Large Ions", Doctor of Philosophy Thesis submitted to Indiana University Department of Chemistry, Dec. 2014, 255 pages.

Kukura, P., et al., "High-speed nanoscopic tracking of the position and orientation of a single virus", Nature Methods 6(12);923-927 (2009).

Latimer, P., "Light Scattering vs. Microscopy for Measuring Average Cell Size and Shape", Biophys. J., 27:117-126 (1979).

Lee, S.F., and Klenerman, D., "Weighing one protein with light", Science 360(6387):378-379 (2018).

Liebel, M., et al., "Ultrasensitive Label-Free Nanosensing and High-Speed Tracking of Single Proteins", Nano Letters 17:1277-1281 (2017).

Lin, Y-H., et al., "Shot-noise limited localization of single 20 nm gold particles with nanometer spatial precision within microseconds", Optics Express 22(8): 12 pages (2014).

Lutomski, C., et al., "Resolving Subpopulations in High and Low-density Lipoproteins", Dept. of Chem, Indiana University, PowerPoint ASMS 2018, 19 pages.

Lutomski, C.A., et al., "Multiple Pathways in Capsid Assembly", JACS 140(17):5784-5790 (2018).

Lutomski, C.A., et al., "Resolution of Lipoprotein Subclasses by Charge Detection Mass Spectrometry", Analytical Chemistry 90(11):6353-6356 (2018).

Mabbett, S.R., et al., "Pulsed Acceleration Charge Detection Mass Spectrometry: Application to Weighing Electrosprayed Droplets", Anal. Chem., 79:8431-8439 (2007).

Makarov, A., et al., "Performance Evaluation of a Hybrid Linear Ion Trap/Orbitrap Mass Spectrometer", Anal. Chem. 78:2113-2120 (2006).

Moerner, W.E., and Fromm, D.P., "Methods of single-molecule fluorescence spectroscopy and microscopy", Review of Scientific Instruments 74(8):3597-3619 (2003).

Morikis, D., and Lambris, J.D., "Physical methods for structure, dynamics and binding in immunological research", Trends in Immunology 25(12): 700-707 (2004).

Morris, J.D., and Payne, C.K., "Microscopy and Cell Biology: New Methods and New Questions", Annual Review of Physical Chemistry 70:199-218 (2019).

(56) References Cited

OTHER PUBLICATIONS

Nie, Z., et al., "Microscopy-Based Mass Measurement of a Single Whole Virus in a Cylindrical Ion Trap", Angewandte Chemie 45:8131-8134 (2006).
Pansieri, J., et al., "Mass and charge distributions of amyloid fibers involved in neurodegenerative diseases: mapping heterogeneity and polymorphism", Chemical Science 9:2791-6 (2018).
Park, J-S., et al., "Label-free and live cell imaging by interferometric scattering microscopy", Chemical Science 9:2690-7 (2018).
Patil, A.A., et al., "High Mass Ion Detection with Charge Detector Coupled to Rectilinear Ion Trap Mass Spectrometer", J. Am. Soc. Mass Spectrom., 28:1066-1078 (2017).
Peng, W-P., et al., "Optical Detection Methods for Mass Spectrometry of Macroions", Mass Spectrometry Reviews 23:443-465 (2004).
Pierson, E. E., et al., "Resolving Adeno-Associated Viral Particle Diversity With Charge Detection Mass Spectrometry", Analytical Chemistry 88:6718-6725 (2016).
Pierson, E., E., et al., "Charge Detection Mass Spectrometry for Single Ions with an Uncertainty in the Charge Measurement of 0.65 e", J. Am. Soc. Spectrom 26:1213-1220 (2015).
Pierson, E.E., et al., "Detection of Late Intermediates in Virus Capsid Assembly by Charge Detection Mass Spectrometry", JACS 136:3536-3541 (2014).
Pierson, E.E., et al., "Detection of Late Intermediates in Virus Capsid Assembly by Charge Detection Mass Spectrometry", Supplementary Figures S1-S7 (2014).
Pierson, Elizabeth E., "Charge Detection Mass Spectrometry: Instrumentation & Applications to Viruses", Dissertation to Indiana University Department of Chemistry (2015) 169 pages.
Piliarik, M., and Sandoghdar, V., "Direct optical sensing of single unlabelled proteins and super-resolution imaging of their binding sites", Nature Communications 5:4495 (2014).
Racke, P., et al., "Detection of small bunches of ions using image charges", Scientific Reports 8:9781 (2018), 10 pages.
Schmidt, H., et al., "Conetrap: A compact electrostatic ion trap", Nuclear Instruments and Methods in Physics Research B 173:523-527 (2001).
Shelton, H., et al., "Electrostatic Acceleration of Microparticles to Hypervelocities", Journal of Applied Physics 31(7):1243-6 (1960).
Sipe, D.M., et al., "Characterization of Mega-Dalton-Sized Naoparticles by Superconducting Tunnel Junction Cryodetection Mass Spectrometry", ACS Nano 12: 2591-2602 (2018).
Smith, J.W., et al., "Image Charge Detection Mass Spectrometry: Pushing the Envelope with Sensitivity and Accuracy", Analytical Chemistry 83(3):950-6 (2011).
Smith, Johnathan, "Charge Detection Mass Spectrometry: Pushing the Limits from Teradaltons to Kilodaltons", Dissertation to Indiana University Department of Chemistry (2011) 175 pages.
Snijder, J., et al., "Defining the Stoichiometry and Cargo Load of Viral and Bacterial Nanoparticles by Orbitrap Mass Spectrometry", JACS 136:7295-7299 (2014).
Sugai, T., "Mass and Charge Measurements on Heavy Ions", Mass Spectrometry 6:S0074 (2017). 18 pages.
Thomas, J.J., et al., "Electrospray ion mobility spectrometry of intact viruses", Spectroscopy 18:31-36 (2004).
Turkowyd, B., et al., "From single molecules to life: microscopy at the nanoscale", Anal Bioanal Chem 408:6885-6911 (2016).
van de Waterbeemd, M., et al., "High-fidelity mass analysis unveils heterogeneity in intact ribosomal particles", Nature Methods [online] doi: 10.1038/nmeth.4147 (2017) 7 pages.
Verschueren, H., "Interference Reflection Microscopy in Cell Biology: Methodology and Applications", J. Cell Sci. 75:279-301 (1985).
Walt, D.R., "Optical Methods for Single Molecule Detection and Analysis", Analytical Chemistry 85:1258-1263 (2013).
Wang, W., and Tao, N., "Detection, Counting, and Imaging of Single Nanoparticles", Analytical Chemistry 86:2-14 (2014).
Yavor, M.I., et al., "Ion-optical design of a high-performance multiple-reflection time-of-flight mass spectrometer and isobar separator", International Journal of Mass Spectrometry 381-382:1-9 (2015).
Young, G., and Kukura, P., "Interferometric Scattering Microscopy" Annual Review of Physical Chemistry, 70:301-22 (2019).
Young, G., et al., "Quantitative mass imaging of single biological macromolecules", Biophysics 360:423-427 (2018).
Zilch, Lloyd W., "Image Charge Detection and Image Charge Detection Mass Spectrometry", Dissertation to Indiana University Analytical Department of the Department of Chemistry (2008) 143 pages.
Schlottmann, F., et al., "A Simple Printed Circuit Board-Based Ion Funnel for Focusing Low m/z Ratio Ions with high kinetic Energies at Elevated Pressure", J. Am. Soc. Mass Spectrom 30:1813-1823 (2019).
Keifer, D.Z., et al., "Acquiring Structural Information on Virus Particles with Charge Detection Mass Sprectrometry" J. Am. Soc. Mass Spectrom. 27:1026-1036 (2016).
Pierson, E.E., et al., "Charge Detection Mass Spectrometry Identifies Preferred Non-Icosahedral Polymorphs in the Self-Assembly of Woodchuck Hepatitis Virus Capsids", J. Mol Biol 428:292-300 (2016).
Elliott, A.G., et al., "Effects of Individual Ion Energies on Charge Measurements in Fourier Transform Charge Detection Mass Spectrometry (FT-CDMS)", J. Am. Soc. Mass Spectrom. 30:946-955 (2018).
Julian, R.R., et al., "Ion Funnels for the Masses: Experiments and Simulations with a Simplified Ion Funnel", J. Am. Soc. Mass Spectrom. 16:1708-1712 (2005).
Patil, A.A., et al., "Linear and Nonlinear Resonance Ejection of High Mass Ions with charge detection rectilinear ion trap mass spectrometer", Journal Pre-proof International Journal of Mass Spectrometry 450:116301 (2020).
International Search Report and Written Opinion for International Application No. PCT/GB2019/050494, dated Aug. 2, 2019, 23 pages.
International Search Report and Written Opinion for International Application No. PCT/US2021/026383, dated Sep. 10, 2021, 17 pages.
Karampini, E., "The Use of Bayesian Statistics in Mass Spectrometry Data—Literature research", Jan. 1, 2015, Retrieved from the Internet: URL:https://esc.fnwi.uva.nl/thesis/centraal/files/f1299028219.pdf retrieved on Jul. 26, 2019].
Bser, T.K., et al., "A Cryogenic Single Nanoparticle Action Spectrometer" Supplementary Material 8 pages, Dec. 2019.
LCMS-9030—Quadrupole Time-of-Flight Liquid Chromatograph Mass Spectrometer, Shimadzu Scientific Instruments (2011).
Maze, J.T., "Charge Detection Mass Spectrometry", pp. 387-401, Dissertation for Indiana University (2005).
International Preliminary Report on Patentability for PCT/US2021/026383, dated Oct. 6, 2022.
Ashcroft, A. E., "Mass spectrometry-based studies of virus assembly", Current Opinion in Virology, 36:17-24, Jun. 1, 2019.
Azzellino, G., et al., "Resonant noise canceling current front-end for high-resolution impedance sensing", IEEE International Instrumentation and Measurement Technology Conference (I2MTC), pp. 1-6, (2018).
Combined Search and Examination Report for United Kingdom Patent Application No. GB2118929.5, dated Jun. 16, 2022.
Combined Search and Examination Report for United Kingdom Patent Application No. GB2118935.2, dated Jun. 13, 2022.
Combined Search and Examination Report for United Kingdom Patent Application No. GB2218465.9, dated Jun. 2, 2023.
Contino, N. C., et al., "Charge detection mass spectrometry for single ions with a limit of detection of 30 charges", International Journal of Mass Spectrometry, vol. 345-347, p. 153-159, (2013).
Greenwood, J.B., et al., "A comb-sampling method for enhanced mass analysis in linear electrostatic ion traps", Rev. Sci. Instrum., 82:043103-12, (2011).
Gustafson, E.L., et al., Accurately Mapping Image Charge and Calibrating Ion Velocity in Charge Detection Mass Spectrometry, J. Am. Soc. Mass Spectrom, 31:2161-2170, (2020).
Heck, M., et al., "An online FT-ICR Penning-trap mass spectrometer for the DPS2-F section of the KATRIN experiment", Nuclear Instruments & Methods in Physics Research. Section A, 757:54-61, Sep. 1, 2014.

(56) References Cited

OTHER PUBLICATIONS

Hogan, J., et al., "Optimized Electrostatic Linear Ion Trap for Charge Detection Mass Spectrometry", Journal of the American Society for Mass Spectrometry, Elsevier Science Inc, 29(10):2086-2095, Jul. 9, 2018.

International Search Report and Written Opinion for International Patent Application No. PCT/GB2021/053426, dated Apr. 12, 2022.

International Search Report and Written Opinion for International Patent Application No. PCT/GB2021/053427, dated Apr. 5, 2022.

International Search Report and Written Opinion for International Patent Application No. PCT/GB2023/050073, dated Apr. 18, 2023.

Invitation to Pay Additional Fees and Where Applicable Protest Fee for International Patent Application No. PCT/IB2022/060398, dated Feb. 13, 2023.

Keifer, Z. D., et al., "Charge detection mass spectrometry: weighing heavier things", Analyst, 142(10):1654-1671, Apr. 26, 2017.

Kenny, DJ et al., "Scanwave: A New Approach to Enhancing Spectral Data on a Tandem Quadrupole Mass Spectrometer", Journal of the American Society for Mass Spectrometry, 21(6):1061-1069, (210), Feb. 6, 2010.

Lohse, S., et al., "A quartz amplifier for high-sensitivity Fourier-transform ion-cyclotron-resonance measurements with trapped ions", Rev. Sci. Instrum., 90:063202-6, (2019).

Lohse, S., et al., "Quartz resonators for penning traps toward mass spectrometry on the heaviest ions", Rev. Sci. Instrum. 91:093202-8, (2020).

Lu, J., et al., "Improved Peak Detection and Deconvolution of Native Electrospray Mass Spectra from Large Protein Complexes", J. Am. Soc. Mass Spectrom., 26(12):2141-2151, Sep. 1, 2015.

Pierson, E. E., et al., "Resolving Adeno-Associated Viral Particle Diversity With Charge Detection Mass Spectrometry", Anal Chem., 88(13): 6718-6725, Jul. 5, 2017.

Search Report for United Kingdom Paten Application No. GB2211029.0, dated Jan. 27, 2023.

Search Report for United Kingdom Patent Application No. GB2107491.9, dated Mar. 10, 2022.

Smith, D. P., et al., "Deciphering Drift Time Measurements from Travelling Wave Ion Mobility Spectrometry—Mass Spectrometry Studies", Eur. J. Mass Spectrom., 15(2):113-130, Apr. 1, 2009.

Todd, A.R. and Jarrold, M.F., "Dramatic Improvement in Sensitivity with Pulsed Mode Charge Detection Mass Spectrometry", Analytical Chemistry, 91(21):14002-14008, (2019).

\* cited by examiner

ION DETECTOR

CROSS-REFERENCE TO RELATED APPLICATION

This application claims priority from and the benefit of U.S. provisional patent application No. 63/007,691 filed on Apr. 9, 2020. The entire content of this application is incorporated herein by reference.

FIELD OF THE INVENTION

The present invention relates generally to analytical instruments such as mass and/or ion mobility spectrometers, and in particular to an ion detector for an analytical instrument such as a mass and/or ion mobility spectrometer.

BACKGROUND

The detection of low fluxes of high molecular weight ions in an analytical instrument such as a mass spectrometer or ion mobility device is challenging. The most common means of detection is to have the ions impact a conversion dynode at high velocity. When the ions impact the dynode they generate secondary electrons and sometimes smaller secondary ions. These secondary processes can be enhanced by ensuring that the ions impact the conversion dynode with as high a kinetic energy as is practical.

Given the same acceleration potential, large ions travel slower than small ions. Thus, beyond a certain molecular weight, the impacting ions generate fewer and fewer secondary particles. As a practical matter, a molecular weight of about 50,000 Daltons is the upper mass limit for the reliable detection of singly charged ions. Multiply charged ions have somewhat higher limits.

The Applicant believes that there remains scope for improvements to ion detectors for analytical instruments such as mass and/or ion mobility spectrometers.

SUMMARY

According to an aspect, there is provided an ion detector comprising:
  a surface configured to receive one or more ions; and
  a detector configured to detect one or more ions by detecting electromagnetic radiation scattered by one or more ions at the surface.

Various embodiments are directed to an ion detector, such as an ion detector for or of an analytical instrument such as a mass and/or ion mobility spectrometer. The ion detector comprises a surface, such as a surface of a transparent substrate, configured to receive one or more ions, such as one or more gas phase ions. The ion detector further comprises a detector, which may comprise or form part of an interference microscope, where the detector is configured to detect one or more ions by detecting electromagnetic radiation (light) scattered by one or more ions at the surface, for example when the one or more ions arrive at (and impact upon) the surface.

The Applicant has recognised that gas phase ions can be detected using interference microscopy, and moreover that this allows high molecular weight ions to be efficiently detected.

It will be appreciated, therefore, that various embodiments provide an improved ion detector.

The surface may be a surface of a transparent substrate.

The ion detector may comprise an electromagnetic radiation (light) source configured to illuminate the surface and/or the substrate with electromagnetic radiation (light). The source may comprise a source of incoherent electromagnetic radiation (light), or a source of coherent electromagnetic radiation (light) such as a laser configured to illuminate the surface and/or the substrate with a laser beam.

The ion detector may be configured such that electromagnetic radiation from the source can be scattered by one or more ions at the surface, for example when one or more ions arrive at (and impact upon) the surface. The detector may be configured to detect one or more ions by detecting electromagnetic radiation from the source that is scattered by one or more ions at the surface.

The ion detector may be configured such that electromagnetic radiation from the source is reflected by the substrate. The detector may be configured to detect electromagnetic radiation from the source that is reflected by the substrate.

The detector may be configured to detect one or more ions by detecting an interference pattern caused by one or more ions at the surface, for example when one or more ions arrive at (and impact upon) the surface.

The detector may be configured to detect one or more ions by detecting an interference pattern caused by interference of electromagnetic radiation (from the source that is) reflected from the substrate and electromagnetic radiation (from the source that is) scattered by one or more ions at the surface, for example when one or more ions arrive at (and impact upon) the surface.

The detector may comprise or may form part of an interference microscope.

According to an aspect, there is provided an ion detector comprising:
  a surface configured to receive one or more ions; and
  an interference microscope configured to detect one or more ions at the surface.

The ion detector may be configured to detect one or more gas phase ions, for example when one or more gas phase ions arrive at (and impact upon) the surface.

According to an aspect, there is provided an analyser, such as a mass analyser or an ion mobility analyser, comprising the ion detector described above.

The analyser may be configured to determine the mass to charge ratio, charge, mass, time of flight, ion mobility and/or collision cross section of one or more ions.

Where the analyser comprises a mass analyser, the mass analyser may comprise a field free or drift region. The surface may be arranged at an exit region of the field free or drift region. The mass analyser may be configured to determine the mass to charge ratio of one or more ions by measuring the time of flight of one or more ions through the field free or drift region.

Where the analyser comprises an ion mobility analyser, the ion mobility analyser may comprise an ion mobility separator, which may be configured to separate ions according to their ion mobility. The surface may be arranged at an exit region of the ion mobility separator. The ion mobility analyser may be configured to determine the ion mobility and/or collision cross section of one or more ions by measuring the drift time of one or more ions through the ion mobility separator.

According to an aspect, there is provided an analytical instrument comprising the ion detector and/or the analyser described above. The analytical instrument may comprise a mass and/or ion mobility spectrometer.

The analytical instrument may further comprise a non-destructive mass analyser. The analytical instrument may comprise one or more devices configured to cause one or more ions analysed by the non-destructive mass analyser to be deposited upon the surface.

According to an aspect, there is provided an analytical instrument comprising:

a non-destructive mass analyser;
a surface; and
one or more devices configured to cause one or more ions analysed by the mass analyser to be deposited upon the surface.

The non-destructive mass analyser may be configured to determine the mass to charge ratio, charge and/or mass of one or more ions without destroying the one or more ions.

The non-destructive mass analysers may comprise a Charge Detection Mass Spectrometry ("CDMS") mass analyser, an ion trap mass analyser, an Ion Cyclotron Resonance ("ICR") mass analyser, a Fourier Transform Ion Cyclotron Resonance ("FTICR") mass analyser, an electrostatic mass analyser arranged to generate an electrostatic field having a quadro-logarithmic potential distribution (an "Orbitrap" mass analyser), a Fourier Transform electrostatic mass analyser, a Fourier Transform mass analyser ("FTMS"), or a Time of Flight (ToF) mass analyser.

The surface may be configured to be removable from the analytical instrument.

The one or more devices may comprise one or more electrodes, such as one or more deflection electrodes.

The one or more devices may be configured to cause ions analysed by the mass analyser to be deposited upon the surface at different positions on or regions of the surface.

For example, the one or more devices may be configured to cause one or more first ions to be deposited at a first position on or within a first region of the surface, and to cause one or more second ions to be deposited at a second different position on or within a second different region of the surface. The one or more devices may be configured to cause one or more third different ions to be deposited at a third different position on or within a third different region of the surface, and so on.

The one or more devices may be configured to cause ions analysed by the non-destructive mass analyser to be deposited upon the surface at different positions on or regions of the surface, such that the position on or region of the surface at which an ion is deposited depends on the mass to charge ratio, charge or mass of the ion.

For example, ions having a first mass to charge ratio, charge and/or mass or a first range of mass to charge ratio, charge and/or mass may be deposited within a first region of the substrate, and ions having a second different mass to charge ratio, charge and/or mass or a second different range of mass to charge ratio, charge and/or mass may be deposited within a second different region of the substrate. Ions having a third different mass to charge ratio, charge and/or mass or a third different range of mass to charge ratio, charge and/or mass may be deposited within a third different region of the substrate, and so on.

According to an aspect, there is provided a method of detecting one or more ions, the method comprising:

detecting one or more ions by detecting electromagnetic radiation scattered by one or more ions at a surface.

The method may comprise detecting one or more ions by detecting electromagnetic radiation scattered by one or more ions when one or more ions arrive at (and impact upon) the surface.

The surface may be a surface of a transparent substrate.

The method may comprise illuminating the surface and/or the substrate with electromagnetic radiation (light), such as a laser beam.

The method may comprise detecting one or more ions by detecting electromagnetic radiation from the source that is scattered by one or more ions at the surface, for example when one or more ions arrive at (and impact upon) the surface.

The method may comprise detecting electromagnetic radiation from the source that is reflected by the substrate.

The method may comprise detecting one or more ions by detecting an interference pattern caused by one or more ions at the surface, for example when one or more ions arrive at (and impact upon) the surface.

The method may comprise detecting one or more ions by detecting an interference pattern caused by interference of electromagnetic radiation (from the source that is) reflected from the substrate and electromagnetic radiation (from the source that is) scattered by one or more ions at the surface, for example when one or more ions arrive at (and impact upon) the surface.

The method may comprise detecting one or more ions using an interference microscope.

According to an aspect, there is provided a method of detecting one or more ions, the method comprising using an interference microscope to detect one or more ions at a surface.

The method may comprise detecting one or more gas phase ions, for example when one or more gas phase ions arrive at (and impact upon) the surface.

According to an aspect, there is provided a method of analysing one or more ions comprising using the method of detecting one or more ions described above to detect one or more ions.

The method may comprise determining the mass to charge ratio, time of flight, ion mobility and/or collision cross section of one or more ions.

The surface may be arranged at an exit region of a field free or drift region of a mass analyser. The method may comprise determining the mass to charge ratio of one or more ions by measuring the time of flight of one or more ions through the field free or drift region.

The method may comprise separating ions according to their ion mobility using an ion mobility separator. The surface may be arranged at an exit region of the ion mobility separator. The method may comprise determining the ion mobility and/or collision cross section of one or more ions by measuring the drift time of one or more ions through the ion mobility separator.

According to an aspect, there is provided a method of mass and/or ion mobility spectrometry comprising the method described above.

The method may further comprise analysing one or more ions using a non-destructive mass analyser. The method may comprise causing one or more ions analysed by the non-destructive mass analyser to be deposited upon the surface.

According to an aspect, there is provided a method of analysing one or more ions, the method comprising:

determining the mass to charge ratio, charge and/or mass of one or more ions using a non-destructive mass analyser;
depositing the one or more ions upon a substrate; and then analysing the one or more ions.

The method may comprise determining the mass to charge ratio, charge and/or mass of one or more ions without destroying the one or more ions.

The non-destructive mass analysers may comprise a Charge Detection Mass Spectrometry ("CDMS") mass analyser, an ion trap mass analyser, an Ion Cyclotron Resonance ("ICR") mass analyser, a Fourier Transform Ion Cyclotron Resonance ("FTICR") mass analyser, an electrostatic mass analyser arranged to generate an electrostatic field having a quadro-logarithmic potential distribution (an "Orbitrap" mass analyser), a Fourier Transform electrostatic mass analyser, a Fourier Transform mass analyser ("FTMS"), or a Time of Flight (ToF) mass analyser.

The method may comprise removing the surface from the analytical instrument (together with the one or more ions deposited thereon) before analysing the one or more ions.

The method may comprise causing ions analysed by the non-destructive mass analyser to be deposited upon the surface at different positions on or regions of the surface.

The method may comprise causing ions analysed by the non-destructive mass analyser to be deposited upon the surface at different positions on or regions of the surface such that the position on or region of the surface at which an ion is deposited depends on the mass to charge ratio, charge or mass of the ion.

The one or more ions may comprise one or more viral capsid ions, one or more exosome ions and/or one or more vexosome ions. Additionally or alternatively, the one or more ions may comprise one or more ions derived from one or more viral capsid ions, one or more exosome ions and/or one or more vexosome ions. For example, the one or more ions may comprise fragment or product ions derived from one or more viral capsid ions, one or more exosome ions and/or one or more vexosome ions.

Analysing the one or more ions may comprise detecting the one or more ions on the substrate. Detecting the one or more ions on the substrate may comprise detecting one or more ions using the method of detecting one or more ions described above.

Analysing the one or more ions may comprise analysing the one or more ions using mass and/or ion mobility spectrometry (so as to determine their mass to charge ratio, charge, mass, ion mobility and/or collision cross section).

Analysing the one or more ions may comprise determining one or more additional properties of the one or more ions (one or more properties other than mass to charge ratio, charge and/or mass).

Analysing the one or more ions may comprise analysing the one or more ions using any one or more of: (i) immunolabelling; (ii) anti-body labelling; (iii) amplification; (iv) polymerase chain reaction (PCR); (v) genetic analysis; (vi) microscopy; and/or (vii) fluorescence microscopy.

BRIEF DESCRIPTION OF THE DRAWINGS

Various embodiments will now be described, by way of example only, and with reference to the accompanying drawings in which.

DETAILED DESCRIPTION

Figure 1:
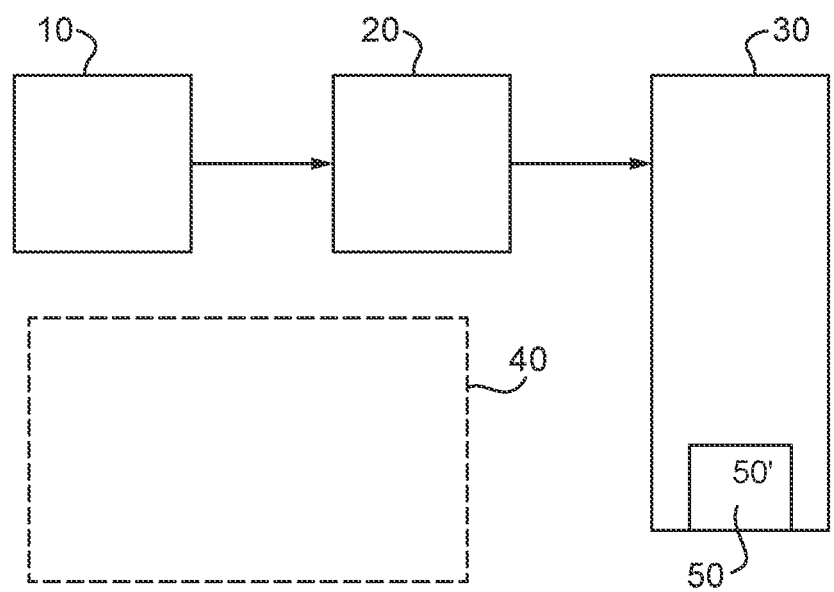
FIG. 1 shows schematically an analytical instrument in accordance with various embodiments.

The detection of low fluxes of high molecular weight ions in an analytical instrument such as a mass spectrometer or ion mobility device is challenging. The most common means of detection is to have the ions impact a conversion dynode at high velocity. When the ions impact the dynode they generate secondary electrons and sometimes smaller secondary ions. These secondary processes can be enhanced by ensuring that the ions impact the conversion dynode with as high a kinetic energy as is practical.

Given the same acceleration potential, large ions travel slower than small ions. Thus, beyond a certain molecular weight, the impacting ions generate fewer and fewer secondary particles. As a practical matter, a molecular weight of about 50,000 Daltons is the upper mass limit for the reliable detection of singly charged ions. Multiply charged ions have somewhat higher limits.

Recently, there has been increasing interest in detecting relatively large particles such as viral capsids and exosomes by mass and/or ion mobility spectrometry.

The current, primary means for such analyses is a technique called Charge Detection Mass Spectrometry ("CDMS"). In this technique, ions are typically oscillated in an electrostatic trap. On each oscillation, the ions pass through a tubular electrode connected to a low noise electronic amplifier. Each time an ion passes through this electrode, it induces an image charge on the electrode and thus, a transient electrical signal that can be recorded. The signals from each pass may optionally then be averaged together to improve the signal to noise ratio. The amplitude of this averaged signal (or of each of the signals from each pass) is proportional to the charge on the ion, while the frequency of the signal provides a measure of the mass-to-charge ratio of the ion.

However, these techniques are incompatible with various forms of mass and ion mobility spectrometry. For example, Matrix Assisted Laser Desorption Ionisation (MALDI) can produce charged virus particles, but there is no conventional way to directly detect the arrival of such ions at the end of a flight path.

In accordance with various embodiments, the Applicant has now recognised that interference microscopy can be used to detect high molecular weight ions in an analytical instrument, such as a mass and/or ion mobility spectrometer. Interference microscopy can be used to detect the light scattered by one or more ions when the one or more ions arrive at and stick to the surface of an optically transparent substrate. These techniques are compatible with forms of mass and/or ion mobility spectrometry that measure the drift time or flight time of ions.

Various embodiments are therefore directed to an ion detector such as an ion detector for or of an analytical instrument such as a mass and/or ion mobility spectrometer. The ion detector comprises a surface such as a surface of a transparent substrate (a transparent plate), configured to receive one or more ions such as one or more gas phase ions. The ion detector may further comprise an interference microscope configured to detect one or more ions that are received at (that impact upon) the surface. The ion detector comprises a detector configured to detect one or more ions by detecting electromagnetic radiation scattered by one or more ions at the surface, for example when the one or more ions arrive at (and impact upon) the surface.

FIG. 1 shows schematically an analytical instrument such as a mass and/or ion mobility spectrometer in accordance with various embodiments.

As shown in FIG. 1, the analytical instrument may comprise an ion source 10, optionally one or more functional components 20 that are arranged downstream from the ion source 10, and an analyser 30 that is arranged downstream from the ion source 10 and downstream from the one or more functional components 20.

As illustrated by FIG. 1 the analytical instrument may be configured such that ions can be provided by (sent from) the ion source 10 to the analyser 30 via the one or more functional components 20.

The ion source 10 may be configured to generate ions, for example by ionising an analyte. The ion source 10 may comprise any suitable ion source such as an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; (xxviii) a Laser Ablation Electrospray Ionisation ("LAESI") ion source; (xxix) a Surface Assisted Laser Desorption Ionisation ("SALDI") ion source; (xxx) a Low Temperature Plasma ("LTP") ion source; (xxxi) a Helium Plasma Ionisation ("HePI") ion source; (xxxii) a Rapid Evaporative Ionisation Mass Spectrometry ("REIMS") ion source; and (xxxiii) a Laser Assisted Rapid Evaporative Ionisation Mass Spectrometry ("LA-REIMS") ion source.

The analytical instrument may comprise a chromatography or other separation device (not shown in FIG. 1) upstream of (and coupled to) the ion source 10. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

Where present, the one or more functional components 20 may comprise any suitable such components, devices and functional elements of an analytical instrument (mass and/or ion mobility spectrometer).

For example, in various embodiments, the one or more functional components 20 comprise one or more ion guides, one or more ion traps, and/or one or more mass filters, for example which may be selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The one or more functional components 20 may comprise an activation, collision, fragmentation or reaction device configured to activate, fragment or react ions.

Where present, the activation, collision, fragmentation or reaction device may comprise any suitable activation, collision, fragmentation or reaction device. For example, the activation, collision, fragmentation or reaction device may be selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and/or (xxix) an Electron Ionisation Dissociation ("EID") fragmentation device.

The one or more functional components 20 may comprise an ion mobility separator configured to separate ions according to their ion mobility. The ion mobility separator may comprise a linear ion mobility separator, or a closed loop (cyclic) ion mobility separator.

The one or more functional components 20 may optionally comprise a non-destructive mass analyser (which may be provided upstream of and in addition to the "final" analyser 30), such as, for example, a Charge Detection Mass Spectrometry ("CDMS") mass analyser, an ion trap mass analyser, an Ion Cyclotron Resonance ("ICR") mass analyser, a Fourier Transform Ion Cyclotron Resonance ("FTICR") mass analyser, an electrostatic mass analyser arranged to generate an electrostatic field having a quadro-logarithmic potential distribution (an "Orbitrap" mass analyser), a Fourier Transform electrostatic mass analyser, a Fourier Transform mass analyser ("FTMS"), a Time of Flight ("ToF") mass analyser, and the like.

The analyser 30 may be configured to analyse ions, so as to determine (measure) one or more of their physicochemical properties, such as their mass to charge ratio, time of flight, (ion mobility) drift time and/or collision cross section (CCS). To do this, as will described in more detail below, the analyser 30 comprises an ion detector 50.

The analytical instrument may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

It should be noted that FIG. 1 is merely schematic, and that the analytical instrument may (and in various embodiments does) include other components, devices and functional elements to those shown in FIG. 1.

As shown in FIG. 1, the analytical instrument may comprise a control system 40 that may be configured to control the operation of the analytical instrument, for example in the manner of the various embodiments described herein. The control system may comprise suitable control circuitry (a controller) that is configured to cause the instrument to operate in the manner of the various embodiments described herein. The control system may comprise suitable processing circuitry (a processor) configured to perform any one or more or all of the necessary processing and/or post-processing operations in respect of the various embodiments described herein. In various embodiments, the control system may comprise a suitable computing device, a microprocessor system, a programmable FPGA (field programmable gate array), and the like.

The analyser 30 may comprise a mass analyser (that may be configured to determine the mass to charge ratio or time of flight of ions) such as a Time of Flight mass analyser and/or an ion mobility analyser (that may be configured to determine the ion mobility (drift time) or collision cross section (CCS) of ions).

Where the analyser 30 comprises a mass analyser, the mass analyser may comprise any suitable mass analyser such as a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; (xiv) a linear acceleration Time of Flight mass analyser; and (xv) a multi-reflecting Time of Flight ("mr-ToF") mass analyser.

In various particular embodiments, the analyser 30 comprises a Time of Flight mass analyser such as an orthogonal acceleration Time of Flight mass analyser, a linear acceleration Time of Flight mass analyser, or a multi-reflecting a Time of Flight ("mr-ToF") mass analyser. The Time of Flight mass analyser may optionally include one or more reflectrons and/or one or more ion mirrors.

In these embodiments, the analyser 30 may comprise an acceleration (pusher and/or puller) electrode, an acceleration region, and a field free or drift region. The ion detector 50 may be arranged at an end region of the field free or drift region.

One or more ions may be arranged to enter the acceleration region, where they may be driven into the field free or drift region by application of a voltage to the acceleration electrode.

Each of the one or more ions may be accelerated to a velocity determined by the energy imparted by the voltage pulse and the mass to charge ratio of each of the one or more ions. An ion having a relatively low mass to charge ratio will achieve a relatively high velocity and reach the ion detector 50 in a shorter time than an ion having a relatively high mass to charge ratio.

Each ion may arrive at the ion detector 50 after a time determined by its velocity and the distance travelled, which enables the mass to charge ratio of the ion to be determined. Each ion or groups of ions arriving at the detector 50 is sampled by the detector 50, and the detector 50 may produce a signal. A processor may then determine (from the signal) a value indicative of the time of flight and/or mass-to-charge ratio ("m/z") of the ion or group of ions. Data for multiple ions may optionally be collected and combined to generate a Time of Flight ("ToF") spectrum and/or a mass spectrum.

Where the analyser 30 comprises an ion mobility analyser, the analyser 30 may comprise an ion mobility separator, and the ion detector 50 may be arranged at an end region of the ion mobility separator.

The ion mobility separator may be configured to separate ions according to their ion mobility. Ions may be separated according to their ion mobility such that ions having different ion mobilities (collision cross sections) arrive at the ion detector 50 at different times, for example such that an ion with a relatively high ion mobility arrives at the ion detector 50 in less time than an ion with a relatively low ion mobility (or such that an ion with a relatively low value of ion mobility arrives at the ion detector 50 in less time than an ion with a relatively high value of ion mobility).

The separator may comprise any suitable ion mobility separator that is configured to separate ions according to their ion mobility.

The ion mobility separator may be configured such that ions are confined within the ion mobility separator, for example in a radial direction, where the radial direction is orthogonal to the direction of travel of ions through the ion mobility separator. According to various embodiments, a radio frequency (RF) voltage may be applied to the electrodes in order to confine ions (radially) within the ion mobility separator (so as to generate a pseudo-potential well that acts to confine ions within the ion mobility separator), and the ion mobility separator may comprise an RF voltage source configured to apply the RF voltage to the electrodes. Opposite phases of the RF voltage may be applied to adjacent electrodes, for example.

According to various embodiments, a DC voltage gradient may be applied to the electrodes in order to urge ions though the ion mobility separator (that is, so as to generate an (axial) electric field that acts to urge ions though the ion mobility separator), and the ion mobility separator may comprise a DC voltage source configured to apply the DC voltage gradient to the electrodes. Different DC voltages may be applied to different (axially spaced) electrodes so as to create a DC voltage gradient that urges ions within the ion mobility separator (in an axial direction).

Additionally or alternatively, a travelling DC voltage may be applied to the electrodes in order to urge ions though the ion mobility separator. That is, a DC voltage may be successively applied to different (axially spaced) electrodes so as to create a travelling DC potential barrier that travels in a direction so as to urge ions within the ion mobility separator to move through the ion mobility separator.

It would also be possible to use a gas flow to urge ions through the ion mobility separator against an electric field so as to separate the ions according to their ion mobility.

An ion may arrive at the ion detector 50 after a time determined by the ion mobility (collision cross section) of the ion, which enables the ion mobility (collision cross section) of the ion to be determined. Each ion or groups of ions arriving at the detector 50 is sampled by the detector 50, and the detector 50 may produce a signal. A processor may then determine (from the signal) a value indicative of the drift time and/or ion mobility (collision cross section) of the ion or group of ions. Data for multiple ions may optionally be collected and combined to generate an ion mobility spectrum.

As described above, in various embodiments, the ion detector 50 comprises a surface such as a surface of a transparent substrate (a transparent plate), configured to receive one or more ions such as one or more gas phase ions. The ion detector 50 further comprises a detector configured to detect one or more ions by detecting electromagnetic radiation (light) scattered by the one or more ions at the surface, for example when the one or more ions arrive at (and impact upon) the surface.

The detector may comprise or may form part of an interference microscope. The Applicant has recognised that gas phase ions can be detected using interference microscopy, and moreover that this allows high molecular weight ions to be efficiently detected.

The surface may be arranged within the analyser 30 of the analytical instrument so as to receive one or more ions to be detected. The surface may accordingly be arranged within an ambient pressure region, a sub-ambient pressure region or a vacuum region of the analytical instrument.

For example, where as described above, the analyser 30 comprises a Time of Flight mass analyser, the surface may be arranged at an end region of a field free or drift region, such that one or more ions being analysed by the Time of Flight mass analyser will impact upon the surface after travelling through the field free or drift region.

Where, as described above, the analyser 30 comprises an ion mobility analyser, the surface may be arranged at an end region of the ion mobility separator, such that one or more ions being analysed by the ion mobility analyser will impact upon the surface after travelling through the ion mobility separator.

In various particular embodiments, the surface comprises a surface of a transparent substrate such as a transparent plate. Thus, the ion detector may comprise a transparent substrate configured to receive one or more ions, and the detector (the interference microscope) may be configured to detect one or more ions by detecting one or more ions on (received at) a surface of the transparent substrate.

According to various embodiments, the surface (substrate) may be electrically conductive. For example, the surface may be formed from a material having a high (but finite) resistivity. Forming the substrate from an electrically conductive material allows charge from one or more ions that impact the surface to dissipate, so as to avoid charge building up on the surface (that might otherwise prevent one or more further ions from reaching the surface or distort their path).

The surface (substrate) may be formed from any suitable material. For example, the substrate may be formed from glass or a transparent plastic such as for example PMMA and the like.

Additionally or alternately, the substrate may comprise a composite. For example, an (thin) electrically conductive film may be deposited on one surface of an insulating material. Such a composite substrate may be positioned, for example, such that ions are received at (and land on) the conductive film.

The ion detector 50 further comprises a detector configured to detect one or more ions by detecting electromagnetic radiation (light) scattered by one or more ions when the one or more ions are received at the surface.

The detector may be a detector of an interference microscope. Thus, the ion detector may comprise an interference microscope, such as an interferometric scattering microscope, configured to detect one or more ions that are received at (that impact upon) the surface.

The (interference microscope of the) ion detector may comprise an electromagnetic radiation (light) source 50', which may be arranged to illuminate the surface and/or the substrate with electromagnetic radiation (light). The source 50' may be a coherent radiation source such as a laser. Thus, the source 50' may be configured to illuminate the surface and/or the substrate with coherent radiation such as a laser beam. Alternatively, the source 50' may be an incoherent radiation source. Where the source 50' comprises a coherent source such as a laser, the spatial and/or temporal coherence of the laser beam may optionally be reduced.

The detector may be an electromagnetic radiation (light) detector, such as an image sensor (of a camera) or a point-like detector. The detector may comprise any suitable such detector, such as for example, a charge-coupled device (CCD), a photodiode, and the like.

The detector may be arranged to receive (and detect) electromagnetic radiation 59' (light) (produced by the source) reflected from the (transparent) substrate. The detector may also be arranged to receive (and detect) any electromagnetic radiation 59 (light) (produced by the source) scattered from one or more ions received at the surface of the substrate.

To do this, the (interference microscope of the) ion detector may further comprise one or more optical components arranged between the substrate, the source and the detector. The one or more optical components may include one or more lenses, such as an objective lens (which may be the one or more lenses disposed closest to (e.g. in front of) the substrate), a condenser lens, a tube lens, and so on. The one or more optical components may also include one or more mirrors, one or more beam splitters such as one or more polarising beam splitters, one or more wave plates, and so on.

The one or more optical components may be configured to direct electromagnetic radiation (light) from the source onto the substrate, and to collect electromagnetic radiation 59' reflected from the substrate and any electromagnetic radiation 59 scattered by one or more ions received at the surface of the substrate, and to direct the collected electromagnetic radiation (light) to the detector.

The (interference microscope of the) ion detector may be configured such that the electromagnetic radiation 59 (light) scattered by an ion received at (close to or on) the surface of the substrate will interfere with the electromagnetic radiation 59' (light) reflected by the substrate. This may be so as to produce an interference pattern. The detector may be configured to detect this interference pattern so as to detect the ion.

Thus, the detector may be configured to detect an ion at the surface by detecting an interference pattern caused by the ion arriving at the surface (which may be caused by interference of the electromagnetic radiation 59' (light) (produced by the source) reflected by the substrate and the electromagnetic radiation (light) 59 (produced by the source) scattered by the ion received at the surface of the substrate).

Thus, in various embodiments, the detector is configured to detect one or more ions by detecting an interference pattern due to one or more ions arriving at the surface.

This may be achieved in any suitable manner. For example, the (interference microscope of the) ion detector may comprise a processor, such as an image processor, configured to detect an interference pattern in one or more images produced by the detector.

Various embodiments accordingly relate to an ion detector configured to detect the arrival of an ion, such as a higher molecular weight ion or charged particle, for example travelling in an ambient pressure atmosphere, a sub-ambient pressure atmosphere or a vacuum, when the ion deposits on an optically transparent substrate, by measuring the light scattered by the ion after it arrives at the substrate.

Various embodiments are broadly applicable to various forms of mass spectrometry and ion mobility spectrometry (as described above).

Figure 2:
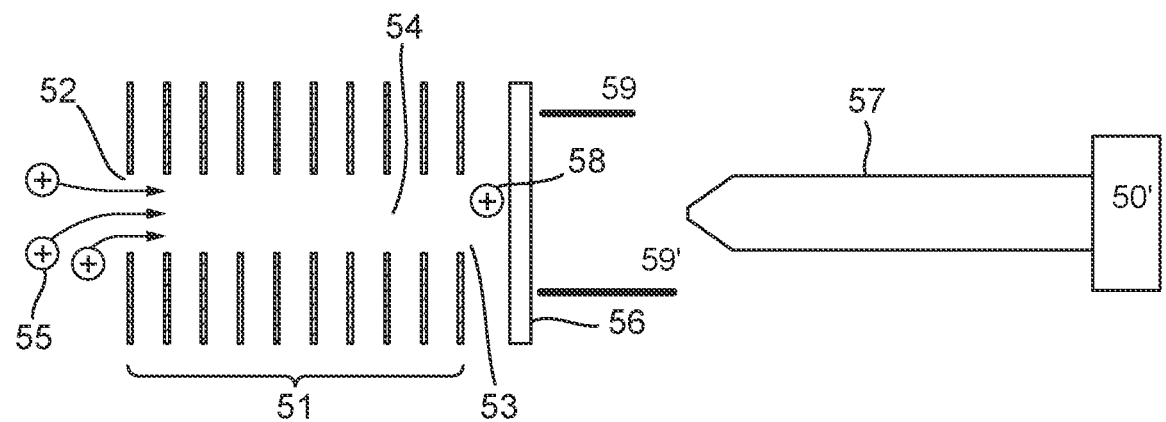
FIG. 2 shows schematically an ion mobility spectrometer in accordance with various embodiments.

FIG. 2 shows a first illustrative embodiment. Here, the ion detector of various embodiments is used to detect the arrival of ions in an atmospheric pressure ion mobility device.

As shown in FIG. 2, the ion mobility spectrometer comprises an ion mobility separator and an ion detector. The ion mobility separator may comprise a drift tube 51, which may comprise an ion entrance end 52 and an ion exit end 53. The ion exit end 53 may be axially downstream of the ion entrance end 52.

The drift tube 51 may comprise a plurality of electrodes such as a plurality of ring electrodes. The electrodes may be arranged in series along an axis of the drift tube 51.

In various embodiments, ions 55 may be pulsed into the drift tube 51, for example by applying a pulsed voltage to an external electrode (not shown).

As described above, one or more DC voltages may be applied to the electrodes, so as to generate an electric field along an axis of the drift tube 51. The electric field may comprise a DC voltage gradient, for example such that the electric field varies linearly along an axis of the drift tube 51 from a high electric field at the ion entrance end 52 to a low electric field at the ion exit end 53. Alternatively, the one or more DC voltages may comprise one or more travelling DC voltage waves.

The voltages may be configured to urge ions along the axial length of the ion mobility separator. For example, the polarity of the voltages may be chosen such that ions entering the drift tube 51 at the ion entrance end 52 experience an electrostatic force driving them along an axis of the drift tube 51 towards the ion exit end 53.

In various embodiments, the ion mobility separator may be filled with a drift gas 54. The drift gas may be static. Alternatively, the drift gas 54 may be introduced at the ion exit end 53 of the drift tube 51, for example such that the drift gas 54 flows from the ion exit end 53 of the drift tube to the ion entrance end 52, for example such that the drift gas 54 flows in a direction substantially opposite to the flow of ions along the axis of the drift tube 51.

In various other embodiments, the drift gas 54 may be introduced at the ion entrance end 52 of the drift tube 51, such that the drift gas 54 flows from the ion entrance end 52 of the drift tube 51 to the ion exit end 53, for example such that the drift gas 54 flows in a direction substantially with the flow of ions along an axis of the drift tube 51 so as to urge ions along the length of the separator. In these embodiments, the electric field may be arranged to oppose the flow of drift gas 54.

In general, ions of different species, having different ion mobilities (collision cross sections), will experience different viscous forces within the drift tube 51. As such, ions of different species, having different ion mobilities (collision cross sections) will travel along the axis of the drift tube 51 with different velocities. Because they have different drift velocities, the ions of different species will arrive at the exit end 53 at different times.

In known arrangements, the arriving ions impact a collector plate connected to a sensitive electrometer, producing an electric current pulse that can be measured. The intrinsic limitations of electrometer devices, however, set a limit on the smallest current pulse that can be measured and hence a lower limit on the sample size that can be detected.

In contrast, in various embodiments, the arriving ions are caused to impact a transparent substrate 56.

For example, as shown in FIG. 2, an ion 58 may be deposited on the substrate 56. An interference microscope 57 may then be used to detect the ion 58 of the substrate 56 (as described above). The use of an interference microscope 57 can allow the arrival of each individual ion to be detected (provided that the ion flux is not too high). This means that the device is much more sensitive than an electrical collecting plate.

Figure 3:
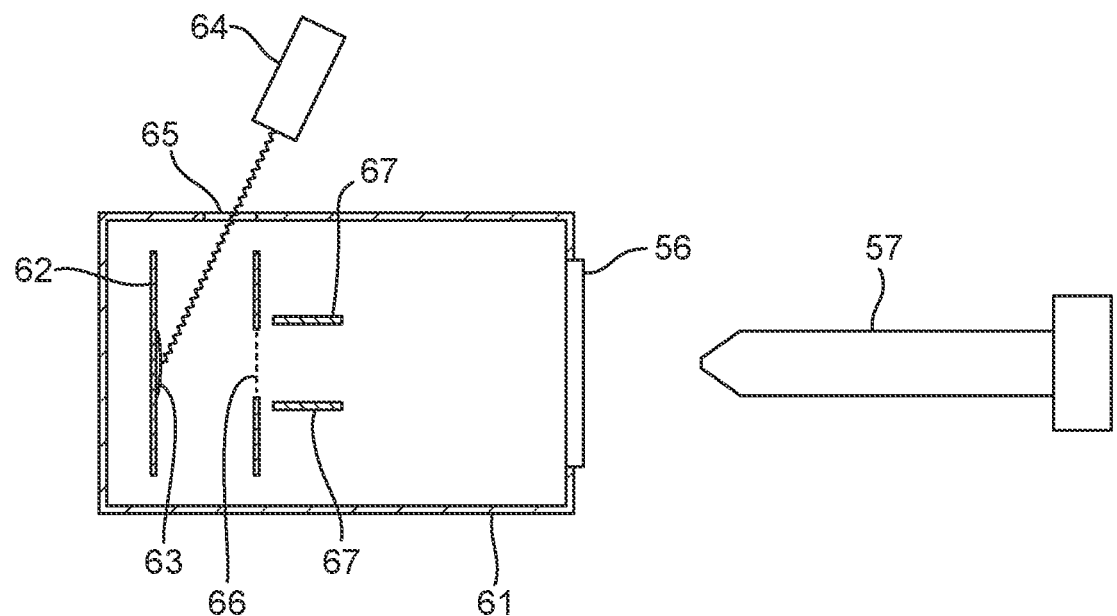
FIG. 3 shows schematically a Matrix-Assisted Laser Desorption-Ionisation Time of Flight ("MALDI-ToF") mass spectrometer in accordance with various embodiments.

A second illustrative embodiment is depicted in FIG. 3. Here, the ion detector of various embodiments may be used to detect ions such as, for example, large ions or charged particles such as virus particles or exosomes, that are generated in a Matrix-Assisted Laser Desorption-Ionization (MALDI) Time-of-Flight (ToF) mass spectrometer (MALDI-ToF).

As shown in FIG. 3, the mass spectrometer may comprise a vacuum chamber 61. The vacuum chamber 61 may be pumped by one or more vacuum pumps (not shown).

The mass spectrometer may comprise a sample holder/substrate 62, which may be arranged within the chamber 61. A sample 63 may be embedded in a matrix upon a surface of the sample holder/substrate 62.

The mass spectrometer may further comprise a laser 64, such as a pulsed laser. The laser 64 may be configured to produce a laser beam with an appropriate wavelength that is absorbed by the matrix.

The laser 64 may be located outside the vacuum chamber 61. Thus, the vacuum chamber 61 may further comprise a window 65, to allow the laser beam of the laser 64 to pass into the vacuum chamber 61.

In operation, energy from the (pulsed) laser may be absorbed by the matrix so as to desorb and ionize the sample 63 so as to generate ions.

The ions may then be accelerated through an electrical potential difference, for example using a grid electrode 66, and may pass into a flight tube. Since the ions are all given the same energy, bigger ions travel more slowly than smaller ions.

The ions are detected when they arrive at the end of the flight tube. Ions may arrive at the ion detector after a time determined by their velocity and the distance travelled, which enables the mass to charge ratio of the ions to be determined (as described above).

As also described above, conventional detectors are inadequate for detecting large particles such as high molecular weight ions.

In accordance with various embodiments, the mass spectrometer comprises an optically transparent substrate 56, which is configured to receive ions. The optically transparent substrate 56 may be a window of the vacuum system. This allows the arrival of the ions to be detected by an interference microscope 57 (as described above).

The Applicant has accordingly recognised that by replacing the conventional detecting means with an optically transparent substrate 56, the arrival of the ions can be detected using interference microscopy. In particular, the Applicant has recognised that an interference microscope can be used to directly detect the arrival of large ions or charged particles such as charged virus particles or exosomes that are produced by MALDI, for example at the end of their flight path.

As also shown in FIG. 3, the analytical instrument may further comprise one or more devices configured to cause one or more ions to be deposited upon the surface. The one or more devices may comprise one or more electrodes, such as one or more deflection electrodes 67.

The one or more devices may be configured to cause ions to be deposited upon the surface at different positions or regions of the surface. For example, the one or more devices may be configured to cause one or more first ions to be deposited at a first position on or within a first region of the surface, and to cause one or more second ions to be deposited at a second different position on or within a second different region of the surface. The one or more devices may be configured to cause one or more third different ions to be deposited at a third different position on or within a third different region of the surface, and so on.

One or more voltages, such as one or more ramped deflection voltages, may be applied to each of the one or more deflection electrodes 67, for example so as to deflect ions so as to cause the position on the surface at which ions arrive to be changed with time. In various embodiments, each of the one or more ramped deflection voltages 67 may be initiated and synchronised with the laser pulse. This may allow ions to be deposited at different positions on the substrate 56, for example so as to increase the ion detecting capacity of the ion detector.

In various embodiments, the ion detector may further comprise one or more devices configured to clean the surface, for example periodically or otherwise. This may allow one or more previously detected ions to be removed, and/or the surface of the transparent substrate to be cleaned prior to first use.

The one or more devices may be configured to clean the in any suitable manner. For example, the surface may be cleared using ion bombardment, a glow discharge, and the like.

Various further embodiments are directed to a method of analysing ions such as large molecular weight ions.

As described above, mass analysers can be used to determine the mass to charge ratio of ions. Although this information is very useful to an analyst in determining the chemical composition of a sample, additional information may be desired.

For example, viral capsids have recently found use in therapeutic techniques such as in gene therapy. In these techniques, a desired DNA (or RNA) sequence is inserted into a viral capsid. Analysis of the mass to charge ratio of a resulting viral capsid can provide information indicating whether or not the insertion of the desired sequence has been successful (for example, where the viral capsid has an expected mass to charge ratio and/or molecular weight), partially successful or unsuccessful (for example, where the viral capsid has an unexpectedly low mass to charge ratio and/or molecular weight).

However, this analysis may not provide the analyst with additional desired information, such as for example the presence and/or nature of impurities within a viral capsid. Impurities such as partial or incorrect DNA (or RNA) sequences can reduce the efficacy of the therapeutic technique, and can even be dangerous to a patient.

It is therefore desirable to be able to determine additional information regarding an ion (such as a viral capsid ion) under analysis.

In this regard, the Applicant has recognised that some mass analysis techniques, such as in particular, Charge Detection Mass Spectrometry ("CDMS"), are non-destructive. That is, analysis of an ion (so as to determine its mass to charge ratio, charge and/or mass) does not result in destruction of the ion Furthermore, the Applicant has recognised that an ion that has been analysed by such a technique can be deposited on a surface, such as a surface of a substrate. This allows the ion or analyte derived from the ion to then be subjected to further analysis.

Thus, various embodiments are directed to an analytical instrument comprising a non-destructive mass analyser (that may be configured to determine the mass to charge ratio, charge and/or mass of an ion) and a surface. The analytical instrument further comprises one or more devices configured to cause an ion analysed by the mass analyser to be deposited upon the surface, for example for further processing and/or analysis.

The analytical instrument may be configured as desired, for example, as described above with respect to FIG. 1.

In these embodiments, the mass analyser may comprise any suitable non-destructive mass analyser (that is, an analyser configured to determine the mass to charge ratio, charge and/or mass of an ion without destroying the ion). The mass analyser may be configured to analyse one (single) ion at a time, for example so as to determine the mass to charge ratio, charge and/or mass of the (single) ion.

Suitable such non-destructive mass analysers include, for example, a Charge Detection Mass Spectrometry ("CDMS") mass analyser, an ion trap mass analyser, an Ion Cyclotron Resonance ("ICR") mass analyser, a Fourier Transform Ion Cyclotron Resonance ("FTICR") mass analyser, an electrostatic mass analyser arranged to generate an electrostatic field having a quadro-logarithmic potential distribution (an "Orbitrap" mass analyser), a Fourier Transform electrostatic mass analyser, a Fourier Transform mass analyser ("FTMS"), a Time of Flight ("ToF") mass analyser (such as the non-destructive Time of Flight ("ToF") mass analyser described above with respect to FIG. 3), and the like.

For example, one type of ion trap mass analyser that may be used in various embodiments comprises a single nanoparticle mass spectrometer such as described by Esser et al. (A cryogenic single nanoparticle action spectrometer, Esser, Hoffmann, Anderson, Asmis, Review of Scientific Instruments, 90, 125110, 2019) and Howder et al. (Optically detected, single nanoparticle mass spectrometer with prefiltered electrospray nanoparticle source, Howder, Bell, Anders, Review of Scientific Instruments, 85, 014104, 2014). In various embodiments, a hybrid mass analyser, for example that includes light scattering detection of ion oscillation frequency (for example as described by Esser), and that uses an induced charge detection electrode to determine the charge of an ion, may be used.

In various particular embodiments, the mass analyser comprises a Charge Detection Mass Spectrometry ("CDMS") mass analyser.

In these embodiments, the Charge Detection Mass Spectrometry ("CDMS") mass analyser may have any suitable configuration, such as for example the configuration described by Jarrold et al. (Charge detection mass spectrometry for single ions with a limit of detection of 30 charges, Contino Jarrold, International Journal of Mass Spectrometry, 345-347, 153-159, 20).

In various embodiments, the Charge Detection Mass Spectrometry ("CDMS") mass analyser may comprise an electrostatic trap. The electrostatic trap may comprise an ion entrance and/or an ion exit. One or more entrance electrodes may be located at the ion entrance and/or one or more exit electrodes may be located at the ion exit.

The mass analyser may further comprise a tube such as a cylinder within the electrostatic trap, for example at the centre of the trap. The tube may be located along an axis of the electrostatic trap.

The tube may be electrically conductive, and so may be a tubular (cylindrical) electrode. The tube (electrode) may be electrically connected to an amplifier such as a low noise electronic amplifier.

The analytical instrument may be configured to cause one or more ions to enter the electrostatic trap, for example one at a time. The mass analyser may be configured such that, as an ion passes through the tube, it induces an image charge on the tube, resulting in an induced voltage.

In various embodiments, if an ion has sufficient charge, the induced voltage may be distinguishable from background electronic noise in a single pass of the ion through the tube. When an induced voltage is detected, one or more voltages may be applied to (or raised on) the one or more entrance electrodes and/or exit electrodes of the electrostatic trap, for example so as to trap the ion within the electrostatic trap (so as to close the trap).

The mass analyser may be configured to cause the ion to oscillate multiple times, for example back and forth, for example along the axial length of the electrostatic trap. The mass analyser may be configured such that, on each oscillation, the ion passes through the tube. As such, multiple voltage signals may be induced in the tube. The current that flows to produce the image charge may produce a transient electrical signal that may be recorded.

The mass analyser may be configured to average a plurality of the induced voltage signals, so as to provide an averaged induced voltage signal. This may improve the signal to noise ratio of the charge measurement. The mass analyser may be configured to use the dominant frequency component of the averaged induced voltage signal to provide a measurement indicative of the mass to charge ratio of the ion. The mass analyser may be configured to use the amplitude of the averaged induced voltage signal to provide a measurement indicative of the charge on the ion.

More generally, processing of the signal may occur before and/or after averaging. Thus in embodiments, the mass analyser may be configured to use the dominant frequency component of each of the induced voltage signals to provide a measurement indicative of the mass to charge ratio of the ion, and to use the amplitude of each of the induced voltage signals to provide a measurement indicative of the charge on the ion. Each of these measurements may then be averaged, for example so as to provide an averaged mass to charge ratio measurement and/or an averaged charge measurement.

These measurements may be used to determine (to calculate) the mass (molecular weight) of the ion.

In various embodiments, once an ion has been analysed (so as to determine its mass to charge ratio, charge and/or mass), the ion may then be deposited on the surface.

The surface (the substrate) may be arranged within the analytical instrument so as to receive one or more ions that have been analysed by the mass analyser. The surface may be arranged within an ambient pressure region, a sub-ambient pressure region or a vacuum of the analytical instrument.

In these embodiments, the surface may comprise a surface of a substrate such as a plate. The substrate may be a transparent substrate (for example as described above), but need not be transparent (and may be translucent or opaque). The substrate may be configured such that when an ion is deposited upon the substrate, the ion is retained on the substrate. The substrate may comprise a slide such as a microscope slide.

Where the substrate is a transparent substrate, then one or more ions deposited on the substrate may optionally be detected using an interference microscope, for example in the manner described in detail above.

In various particular embodiments, the surface is configured to be removable from the analytical instrument. The surface may be removed from the analytical instrument together with one or more ions deposited thereon, prior to the one or more ions being analysed. This facilitates a greater degree of flexibility and possibility for the subsequent analysis of the one or more ions.

In various embodiments, the analytical instrument comprises one or more devices configured to cause an ion analysed by the mass analyser to be deposited upon the surface. The one or more devices may be configured to control the position upon the surface at which an ion analysed by the mass analyser is deposited.

The one or more devices may comprise one or more electrodes, such as one or more deflection electrodes. The analytical instrument may be configured to apply one or more voltages to one or more of the electrodes in order to control the position upon the surface at which an ion is deposited. The one or more deflection electrodes may be configured to deflect one or more ions so as to control the position on the surface at which ions arrive.

The one or more deflection electrodes may comprise, for example, a first set of one or more electrodes which may be configured to control the position in a first (x) dimension upon the surface at which an ion is deposited, and a second set of one or more electrodes which may be configured to control the position in a second orthogonal (y) dimension upon the surface at which an ion is deposited.

The one or more devices may be configured to cause different ions analysed by the mass analyser to be deposited upon the surface at different positions or regions of the surface. For example, the one or more devices may be configured to cause one or more first ions to be deposited at a first position on or within a first region of the surface, and to cause one or more second ions to be deposited at a second different position on or within a second different region of the surface. The one or more devices may be configured to cause one or more third different ions to be deposited at a third different position on or within a third different region of the surface, and so on.

In various embodiments, ions may be deposited on the surface in an array pattern. A single ion may be deposited at each position in the array.

The one or more devices may be configured to cause an ion analysed by the mass analyser to be deposited upon the surface at a position or within a region, where the region is selected depending on the result of the mass analyser's analysis of the ion, that is, depending on a determined mass to charge ratio, charge and/or mass of the ion. For example, ions having a first mass to charge ratio, charge and/or mass or a first range of mass to charge ratio, charge and/or mass may be deposited within a first region of the substrate, and ions having a second different mass to charge ratio, charge and/or mass or a second different range of mass to charge ratio, charge and/or mass may be deposited within a second different region of the substrate. Ions having a third different mass to charge ratio, charge and/or mass or a third different range of mass to charge ratio, charge and/or mass may be deposited within a third different region of the substrate, and so on.

Thus, in various embodiments, the analytical instrument is configured to cause ions having different mass to charge ratios, charges and/or masses to be deposited on the surface at different positions or regions. In other words, different ions may be spatially separated on the substrate, for example in an array pattern.

Where ions are deposited on the surface in an array pattern, a single ion may be deposited at each position in the array. Alternatively, plural ions, for example which each have the same or similar mass to charge ratio, charge and/or mass, may be deposited at each position in (or region of) the array.

This allows the determined mass to charge ratio, charge and/or mass information to be retained during the further analysis and/or the different ions to be subjected to different further analysis processes.

Figure 4:
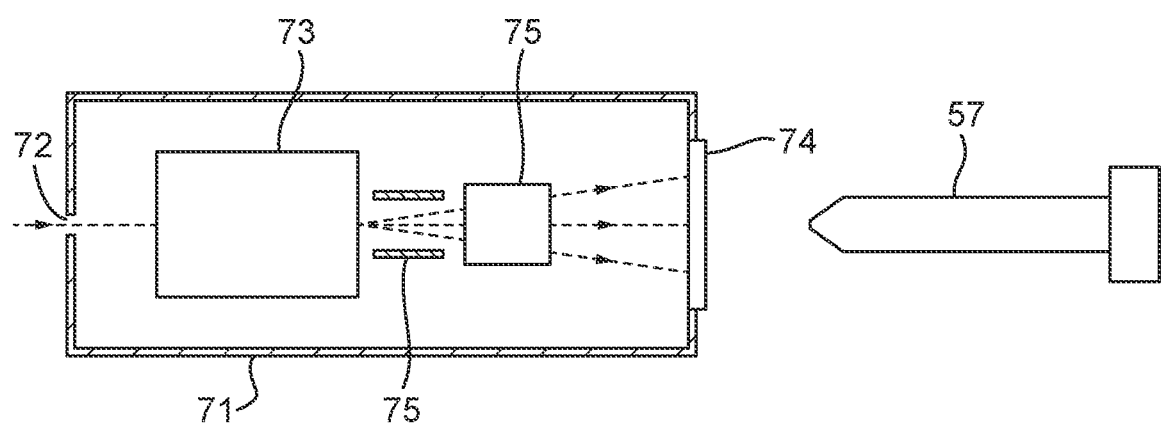
FIG. 4 shows schematically a mass spectrometer in accordance with various embodiments.

FIG. 4 shows an illustrative embodiment in accordance with various embodiments.

As shown in FIG. 4, the analytical instrument may comprise a vacuum chamber 71. The vacuum chamber 71 may comprise a housing. The housing may comprise an aperture 72 at an entrance end of the vacuum chamber 71. Ions may be introduced into the vacuum chamber 71 through the aperture 72.

The ions may be passed to and analysed by a mass analyser 73 (for example in the manner described above). Ions may be analysed one at a time. After analysis, each ion may then be deposited on a substrate 74. This may comprise ejecting an ion from a trapping entity of the mass analyser 73, and directing the ion to be deposited onto the substrate 74.

In the embodiment shown in FIG. 4, the substrate 74 may be (optically) transparent. However, it would be possible for the substrate 74 to be translucent or opaque.

Where the substrate is transparent, an interference microscope 57 may be used to verify that the ion has been deposited on a surface of the substrate 74. The interference microscope 57 may further provide an independent measurement of the molecular weight of the ion. The interference microscope 57 may comprise the interference microscope as described in detail above.

However, the analytical instrument of these embodiments need not comprise an interference microscope, for example if the ion deflecting mechanism is sufficiently well controlled.

The substrate 74 may be removably attached, i.e. such that the substrate 74 may be removed from the analytical instrument.

Where interference microscopy is not used, the substrate 74 need not be part of the wall of the vacuum chamber 71 (as shown in FIG. 4), but may be positioned inside the vacuum chamber 71 in any suitable manner. In these embodiments, a vacuum lock may facilitate removal of the substrate 74.

As described above, in various embodiments, one or more deflection electrodes 75 may be used to deposit each individual ion at a desired position, such as in an array pattern, on the surface of the substrate 74. The precise location a each individual ion is deposited on the substrate 74 may depend on the mass of each individual ion.

The ions that are introduced into the vacuum chamber 71 through the aperture 72 may comprise any suitable ions. For example, the ions may be ions produced by (and directly received from) an upstream ion source 10 (as described above), such as parent or precursor ions.

Additionally or alternatively, the ions may comprise ions derived from ions produced by the ion source 10, such as fragment or product ions of ions produced by the ion source 10. Such fragment or product ions may be produced, for example using the activation, collision, fragmentation or reaction device described above in relation to FIG. 1.

Similarly, the ions may have been processed and/or analysed in any suitable manner by the analytical instrument (before being introduced into the vacuum chamber 71 through the aperture 72). For example, the (parent and/or fragment) ions may have been separated according to their ion mobility using the ion mobility separator (as described above in relation to FIG. 1) and/or mass analysed using the non-destructive mass analyser (as described above in relation to FIG. 1).

For example, in one illustrative embodiment, ions such as capsid and/or exosome ions may be analysed using a non-destructive mass analyser (such as a CDMS mass analyser), and then fragmented, reacted, activated, unfolded and/or denatured. The resulting ions may then be isolated and/or separated according to their ion mobility. The so-separated ions may then be introduced into the vacuum chamber 71 through the aperture 72 for processing by the mass analyser 73 and deposition on the substrate 74, as described above.

In these embodiments, the analytical instrument may comprise a first non-destructive mass analyser (such as a CDMS mass analyser), followed by a activation, collision, fragmentation or reaction cell, followed by a second different non-destructive mass analyser 73 (such as a CDMS mass analyser), where the second non-destructive mass analyser 73 may be configured to perform the arrayed substrate deposition as described above.

Alternatively, a single non-destructive mass analyser (such as CDMS mass analyser) may be used. For example, fragment ions may be sent back from the activation, collision, fragmentation or reaction cell, into the non-destructive mass analyser. This may utilise an ion optical component, such as a quadrupole lens, which may be positioned between the non-destructive mass analyser and the activation, collision, fragmentation or reaction cell, and may be configured to deflect the fragments, for example by 90 degrees towards the deflection plates 75 for arrayed deposition on the substrate 74.

As described above, in various embodiments, one or more ions deposited on the substrate are subjected to further analysis.

Where necessary or desirable for the particular analysis process, the substrate may be removed from the analytical instrument prior to analysing the one or more ions deposited on the substrate. Alternatively, the one or more ions array may be analysed within the analytical instrument.

The further analysis may comprise any suitable analysis technique or techniques. The further analysis may be performed so as to determine information regarding the one or more ions, other than their mass to charge ratio, charge and/or mass.

For example, in various embodiments, the second, different analysis may comprise immunolabeling or antibody-labelling. These techniques may use fluorescently labelled antibodies. The second, different analysis may also or instead comprise genetic or DNA analysis. These techniques may be assisted by amplification techniques such as Polymerase chain reaction (PCR), nucleic acid amplification, and so on. The second, different analysis may also or instead comprise microscopy such as fluorescence microscopy.

In various embodiments, the subsequent analysis may comprise antibody-labelling (which may include fluorescently labelled antibodies), and/or Polymerase chain reaction (PCR) assisted analysis of gene therapy viruses for DNA analysis, and so on.

Embodiments allow populations of viruses or viral capsids (and variants) to be resolved in the above described manner, using the one or more deflection electrodes, and to be deposited on a substrate such as a slide. Spatially resolved species may then be subjected to amplification techniques, such as PCR or non-PCR nucleic acid amplification techniques, for the purpose of characterization of target DNA.

The quality and/or quantity of nucleic acid payload in the viruses or capsids may be assessed in this way. Undesired modifications and/or truncations of DNA payload in genetic medicines (that may be harmful to a patient) can be analysed in this way. This information can be combined with the mass information of the intact viruses or capsids.

As described above, ions may be sorted into different regions on the surface, for example, based on the mass of the ion determined by the upstream mass analysis. In this way, the mass analyser 73 may be used as a selector to isolate and deposit ions, thus serving to increase the amount of material of a given molecular ion for subsequent sample analysis.

This analysis may find particular use, for example, in gene therapy modalities (as described above) which use a preparation (and quality control) of viral capsids, exosomes or vexosomes, which are designed to deliver a corrective piece of DNA to a patient for therapeutic purposes. For example, this analysis of various embodiments may reduce the risk to a patient who may suffer adverse consequences if there are fractions of these preparations that comprise other than the desired DNA sequence.

Due to the amplification power of PCR and similar techniques, only a small amount of sample may be required for such viruses or capsid quality control analysis. While genomic amplification is possible with single molecules, using tens or hundreds of copies of viruses or capsids (such as nucleic acid payload copies) may be preferred for more robust analysis. By combining the information from the non-destructive mass analyser 73 (such as the number of deposited ions) and the nucleic acid quantitation (such as by quantitative polymerase chain reaction (qPCR)) the ratio of empty viruses or capsids to payload laden viruses or capsids in the sample can be estimated.

In various embodiments, the quantitation of DNA deposited on the substrate 74 may be performed using, for example, intercalator fluorescent dyes and fluorescent microscopy.

In cases where, for example, point mutation of viruses (their DNA or RNA) occurs and mass analysis (such as CDMS mass analysis) is unable to distinguish the change due to insufficient mass resolution, collected nucleic acid can be amplified and used to assess the mutation rate of a virus within a narrow (mass to charge ratio selected) class of species.

In various embodiments, the non-destructive mass analysis (such as CDMS mass analysis) may be used as a selector, for example to assign exosomes, capsids, viruses, and so on, to classes, which may be subsequently analysed, for example by mass spectrometry, biochemical nucleic acid methods, fluorescent microscopy, and so on.

Various embodiments accordingly allow an analyst to determine the presence and/or nature of impurities, such as partial or incorrect DNA (or RNA) sequences, within a viral capsid.

In various further embodiments, the desired viral capsids may be recovered (without recovering impurities). The recovered viral capsid may then be used for therapeutic purposes. Various embodiments may accordingly allow purification of viral capsids.

Various alternatives would be possible. For example, although as shown in FIGS. 2 to 4, in some embodiments most (or all) components of the interference microscope 57 (except for the substrate 56, 74) may be arranged outside of a vacuum system (vacuum chamber 61, 71) of the analytical instrument, in various other embodiments some or all of the components of the interference microscope 57 may be arranged within a vacuum system (for example, vacuum chamber 61, 71) of the analytical instrument.

It will be appreciated from the above, that various embodiments provide an improved ion detector and an improved analytical instrument.

Although the present invention has been described with reference to preferred embodiments, it will be understood by those skilled in the art that various changes in form and detail may be made without departing from the scope of the invention as set forth in the accompanying claims.

The invention claimed is:

1. An ion detector comprising:
   a surface of a substrate configured to receive one or more ions; and
   a detector configured to detect one or more ions by detecting electromagnetic radiation scattered by one or more ions at the surface.

2. The ion detector of claim 1, wherein the substrate is transparent to the electromagnetic radiation scattered by said one or more ions.

3. The ion detector of claim 1, further comprising an electromagnetic radiation source configured to illuminate the surface with electromagnetic radiation.

4. The ion detector of claim 1, wherein the detector is configured to detect one or more ions by detecting an interference pattern caused by one or more ions at the surface.

5. The ion detector of claim 1, wherein the detector is configured to detect one or more ions by detecting an interference pattern caused by interference of electromagnetic radiation reflected by the substrate and electromagnetic radiation scattered by one or more ions at the surface.

6. The ion detector of claim 1, wherein the ion detector is configured to detect one or more gas phase ions.

7. An analyser comprising the ion detector of claim 1.

8. The analyser of claim 7, wherein the analyser is configured to determine the mass to charge ratio, charge, mass, time of flight, ion mobility and/or collision cross section of one or more ions.

9. The analyser of claim 7, further comprising a field free or drift region, wherein the surface is arranged at an exit region of the field free or drift region.

10. The analyser of claim 7, further comprising an ion mobility separator, wherein the surface is arranged at an exit region of the ion mobility separator.

11. An analytical instrument comprising the ion detector of claim 1.

12. The analytical instrument of claim 11, further comprising:
- a non-destructive mass analyser; and
- one or more devices configured to cause one or more ions analysed by the non-destructive mass analyser to be deposited upon the surface.

\* \* \* \* \*